(12) United States Patent
Thaimattam et al.

(10) Patent No.: US 9,957,234 B2
(45) Date of Patent: May 1, 2018

(54) POLYMORPHS OF IVACAFTOR, PROCESS FOR ITS PREPARATION AND PHARMACEUTICAL COMPOSITION THEREOF

(71) Applicant: Laurus Labs Limited, Hyderabad (IN)

(72) Inventors: Ram Thaimattam, Hyderabad (IN); Venkata Srinivasa Rao Dama, Hyderabad (IN); Venkata Sunil Kumar Indukuri, Hyderabad (IN); Seeta Rama Anjaneyulu Gorantla, Hyderabad (IN); Satyanarayana Chava, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days. days.

(21) Appl. No.: 15/533,595

(22) PCT Filed: Dec. 9, 2015

(86) PCT No.: PCT/IN2015/000446
§ 371 (c)(1),
(2) Date: Jun. 6, 2017

(87) PCT Pub. No.: WO2016/092561
PCT Pub. Date: Jun. 16, 2016

(65) Prior Publication Data
US 2017/0334860 A1 Nov. 23, 2017

(30) Foreign Application Priority Data

Dec. 9, 2014 (IN) .......................... 6217/CHE/2014

(51) Int. Cl.
*C07D 215/56* (2006.01)

(52) U.S. Cl.
CPC ........ *C07D 215/56* (2013.01); *C07B 2200/13* (2013.01)

(58) Field of Classification Search
CPC .......................... C07D 215/56; C07B 2200/13
See application file for complete search history.

(56) References Cited

U.S. PATENT DOCUMENTS

| 8,410,274 | B2 | 4/2013 | Hurter et al. | |
| 9,809,551 | B2 * | 11/2017 | Akbarali | C07D 215/56 |
| 2013/0281487 | A1 * | 10/2013 | Luisi | A61K 31/47 514/312 |

FOREIGN PATENT DOCUMENTS

WO WO-2013158121 A1 10/2013

* cited by examiner

*Primary Examiner* — D Margaret M Seaman
(74) *Attorney, Agent, or Firm* — Blank Rome LLP

(57) ABSTRACT

The present invention relates to novel polymorphic forms of ivacaftor, process for its preparation and pharmaceutical compositions comprising the same.

52 Claims, 16 Drawing Sheets

POLYMORPHS OF IVACAFTOR, PROCESS FOR ITS PREPARATION AND PHARMACEUTICAL COMPOSITION THEREOF

CROSS-REFERENCE TO RELATED APPLICATIONS

This application is a U.S. national phase of PCT/IN2015/000466, filed Dec. 9, 2015, which claims the benefit of the filing date of Indian Provisional Application No. 6217/CHE/2014, filed on Dec. 9, 2014 entitled "Novel polymorphs of Ivacaftor, process for its preparation and pharmaceutical composition thereof", the content and disclosure of which are incorporated by reference herein.

FIELD OF THE INVENTION

The present invention relates to novel polymorphic forms of Ivacaftor, process for its preparation and pharmaceutical compositions comprising the same.

BACKGROUND OF THE INVENTION

Ivacaftor, also known as N-(2,4-di-tert-butyl-5-hydroxyphenyl)-1,4-dihydro-4-oxoquinoline-3-carboxamide, having the following Formula I:

Formula I

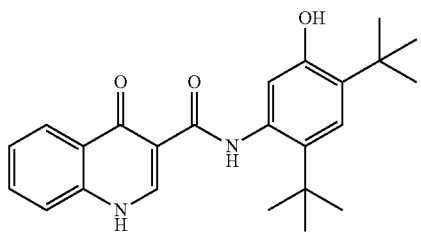

Ivacaftor was approved by FDA and marketed by Vertex pharma for the treatment of cystic fibrosis under the brand name KALYDECO® in the form of 150 mg oral tablets.

WO2006/002421 publication discloses modulators of ATP-binding cassette transporters such as ivacaftor. This patent generally discloses a process for the preparation of modulators of ATP-binding cassette transporters such as quinoline compounds; however, specific process for the preparation of ivacaftor and its solid state details were not specifically disclosed.

WO2007/079139 publication discloses Form A, Form B and amorphous form of ivacaftor characterized by PXRD, DSC and TGA and process for their preparation. Further this publication discloses ethanol crystalate of ivacaftor in example part.

WO2009/038683 publication discloses the solid forms of ivacaftor, which are designated as Form-I (2-methylbutyric acid), Form-II (propylene glycol), Form-III (PEG400.KOAc), Form-IV (lactic acid), Form-V (isobutyric acid), Form-VI (propionic acid), Form-VII (ethanol), Form-VIII (2-propanol), Form-IX (monohydrate), Form-X (besylate Form A), Form-XI (besylate Form B), Form-XII (besylate Form D), Form-XIII (besylate Form E), Form-XIV (besylate Form F), Form-XV (besylate (2:1)), Form-XVI (besylate mono hydrate). This publication also discloses the characterization details like PXRD, DSC and TGA for the above forms and process for their preparation.

WO2011/116397 publication discloses crystalline Form C of ivacaftor, process for its preparation and pharmaceutical composition comprising the same. Also discloses characterization details of Form C, such as PXRD, IR, DSC and $^{13}$CSSNMR.

WO2013/158121 publication discloses solvated forms of ivacaftor, which are designated as Form D (acetonitrile or acetonitrile/water (75/25) solvate), Form E (Methyl ethyl ketone (MEK), MEK/water (90/1), MEK/water (90/10), MEK/water (80/20) solvate), Form F (acetonitrile/water (75/25) solvate), Form G (isopropyl acetate solvate), Form H (isopropyl acetate/water (95/5) solvate), Form I (MEK solvate), Form J (MEK/water (99/1) solvate), Form K (MEK or MEK/water (99/1) or MEK/water (90/10) or MEK/water (80/20) solvate), Form L (isopropyl acetate/water (95/5) solvate), Form M (MEK or MEK/water (99/1) solvate), Form N (MEK/water (90/10) or MEK/water (80/20) solvate), Form O (MEK or MEK/water (99/1) solvate), Form P (MEK/water (90/10) or MEK/water (80/20) solvate), Form Q (MEK/water (80/20) solvate), Form R (acetonitrile solvate), Form S (MEK/water (80/20) solvate), Form T (isopropyl acetate/water (95/5) solvate), Form W (acetonitrile/water (90/10) solvate), Form XX (from 10% water/acetonitrile) and hydrate B (hydrated form). This patent further discloses characterization details like PXRD and TGA for the above forms and process for their preparation.

WO2014/118805 publication discloses crystalline forms of ivacaftor designated as Form D, Form E, Form E1, Form G and Form G'; amorphous ivacaftor designated as Form I and Form II; crystalline ivacaftor solvates such as n-butanol solvate, methanol solvate, propylene glycol solvate, DMF solvate, THF solvate, DMF:ethylacetate solvate. This publication further discloses the process for the preparation of said forms along with their characterization details.

WO2015/070336 publication discloses polymorphic form APO-I and MIBK solvate of ivacaftor along with its characteristic PXRD details, process for its preparation and pharmaceutical composition comprising them.

CN 104725314A publication discloses ivacaftor new polymorph D, which is obtained by crystallization of ivacaftor from acetonitrile/water. This publication further discloses characteristic details such PXRD, IR and DSC of ivacaftor new polymorph D.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predictable solubility profiles. It is desirable to investigate all solid state forms of a drug, including all polymorphic forms and solvates, and to determine the stability, dissolution and flow properties of each polymorphic form.

Polymorphic forms and solvates of a compound can be distinguished in a laboratory by X-ray diffraction spectroscopy and by other methods such as, infrared spectrometry. Additionally, polymorphic forms and solvates of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products.

The discovery of new polymorphic forms and solvates of a pharmaceutically useful compound, like ivacaftor, may provide a new opportunity to improve the performance characteristics of a pharmaceutical product. It also adds to the material that a formulation scientist has available for designing, for example, a pharmaceutical dosage form of a drug with a targeted release profile or other desired characteristic. New polymorphic forms of the ivacaftor have now been discovered and have been designated as ivacaftor Form-L1, Form-L2, Form-L3, Form-L4, Form-L5, Form-L6, Form-L7, Form-L8, Form-L9, Form-L10, Form-L11, Form-L12A, Form-L12B, Form-L13 and Form-L14.

SUMMARY OF THE INVENTION

The present invention provides novel polymorphic forms of ivacaftor, process for their preparation and pharmaceutical compositions comprising one or more of the novel polymorphic forms of ivacaftor.

Accordingly in one aspect, the present invention provides novel polymorphic forms of ivacaftor, herein designated as ivacaftor Form-L1, ivacaftor Form-L2, ivacaftor Form-L3, ivacaftor Form-L4, ivacaftor Form-L5, ivacaftor Form-L6, ivacaftor Form-L7, ivacaftor Form-L8, ivacaftor Form-L9, ivacaftor Form-L10, ivacaftor Form-L11, ivacaftor Form-L12A, ivacaftor Form-L12B, ivacaftor Form-L13 and ivacaftor Form-L14.

In another aspect of the present invention provides a process for preparation of novel polymorphic forms of ivacaftor, which are Form-L1, Form-L2, Form-L3, Form-L4, Form-L5, Form-L6, Form-L7, Form-L8, Form-L9, Form-L10, Form-L11, Form-L12A, Form-L12B, Form-L13 and Form-L14.

In another embodiment, the present invention provides a pharmaceutical composition comprising the crystalline forms of ivacaftor (Form-L1 to Form-L14) described above and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
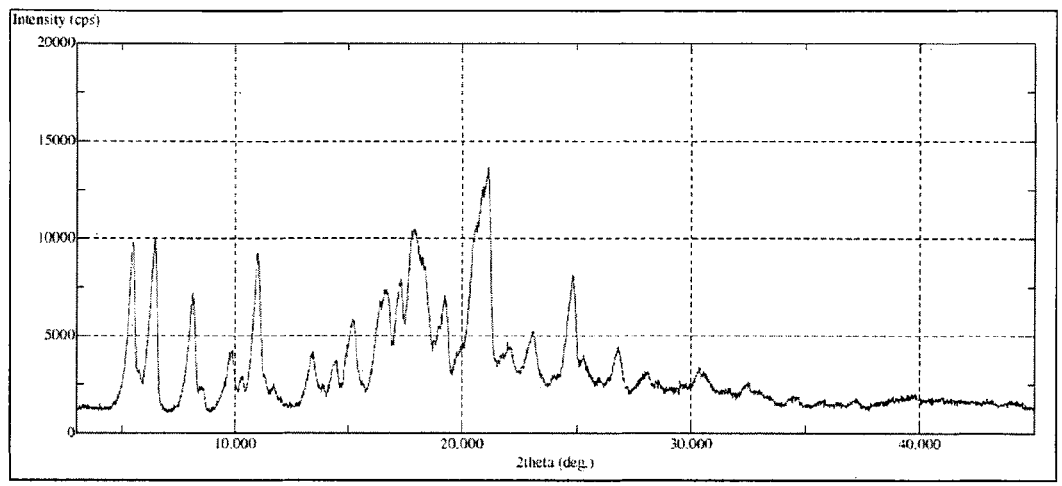
FIG. 1 shows the characteristic powder X-ray diffraction (XRD) pattern of ivacaftor Form-L1.

The present invention provides novel polymorphic forms of ivacaftor, process for their preparation and pharmaceutical compositions comprising one or more of such polymorphic forms.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein in this specification, unless otherwise specified, ivacaftor which is used as a starting material is known in the art and can be prepared by any known methods. The starting ivacaftor may be in any form such as crude obtained directly from the reaction mass, crystalline, amorphous or other forms of ivacaftor, including various hydrates and solvates known in the art as well as the polymorphs or solvates described herein the present invention.

Preferably ivacaftor solvates used as a starting material for the preparation of present invention are selected from ethanol, diisopropylether (DIPE), propanol, cyclopentyl methyl ether (CPME) and methyl tertiarybutylether solvates of ivacaftor and the like or hydrate such as ivacaftor monohydrate. Ivacaftor ethanol solvate used herein as a starting material can be prepared by the methods known in the art, for example as per the method disclosed in U.S. Pat. No. 8,163,772.

The polymorphic forms of ivacaftor of the present invention were characterized by one or more analytical methods, such as X-ray powder diffraction (XRPD) patterns, Differential scanning calorimetry (DSC) and thermo gravimetric analysis (TGA).

The X-Ray powder diffraction can be measured by an X-ray powder Diffractometer equipped with a Cu-anode ($[\lambda]$=1.54 Angstrom), X-ray source operated at 30 kV, 15 mA. Two-theta calibration is performed using NIST SRM 640c Si standard. The sample was analyzed using the following instrument parameters: measuring range=3-40°2θ; step width=0.020°; and scan speed=5°/minute.

All DSC data reported herein were analyzed in hermitically sealed aluminium pan, with a blank hermitically sealed aluminium pan as the reference and were obtained using DSC (DSC Q200, TA instrumentation, Waters) at a scan rate of 10° C. per minute with an Indium standard.

All TGA data reported herein were analyzed using TGA Q500 V 20.13 build 39 in platinum pan with a temperature rise of about 10° C./min in the range of about 30° C. to about 250° C.

In one embodiment, the present invention provides novel polymorphic forms of ivacaftor; which are designated as ivacaftor Form-L1, ivacaftor Form-L2, ivacaftor Form-L3, ivacaftor Form-L4, ivacaftor Form-L5, ivacaftor Form-L6, ivacaftor Form-L7, ivacaftor Form-L8, ivacaftor Form-L9, ivacaftor Form-L10, ivacaftor Form-L11, ivacaftor Form-L12A, ivacaftor Form-L12B, ivacaftor Form-L13 and ivacaftor Form-L14.

In another embodiment, the present invention provides ivacaftor Form-L1.

In another embodiment, the ivacaftor Form-L1 of the present invention is a heptane solvate.

In another embodiment, the present invention provides ivacaftor Form-L1 characterized by a powder X-Ray diffraction (PXRD) pattern substantially in accordance with FIG. 1.

In another embodiment, the present invention provides ivacaftor Form-L1 characterized by a PXRD pattern having one or more peaks at about 5.48, 5.74, 6.46, 8.12, 8.56, 9.82, 10.28, 11.00, 11.70, 13.40, 13.90, 14.38, 15.22, 15.64, 16.38, 16.64, 17.30, 17.80, 18.24, 18.96, 19.22, 20.62, 20.86, 21.12, 21.74, 21.98, 23.06, 23.96, 24.82, 25.30, 25.94, 26.82, 28.08, 28.48 and 30.34±0.2°2θ.

Figure 2:
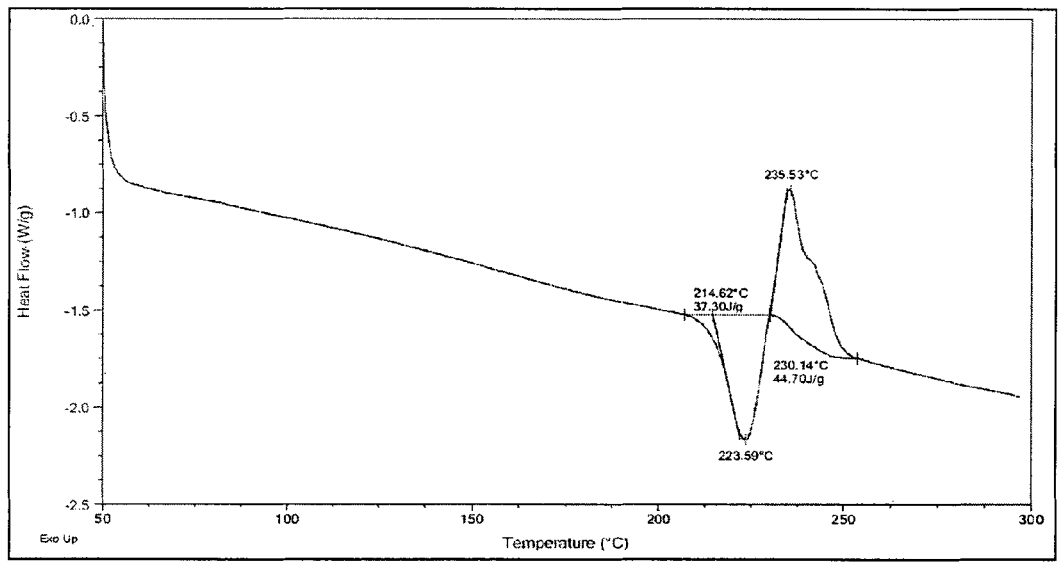
FIG. 2 shows the characteristic differential scanning calorimetric (DSC) thermogram of ivacaftor Form-L1.

In another embodiment, the present invention provides ivacaftor Form-L1 characterized by a differential scanning calorimetry (DSC) substantially in accordance with FIG. 2.

Figure 3:
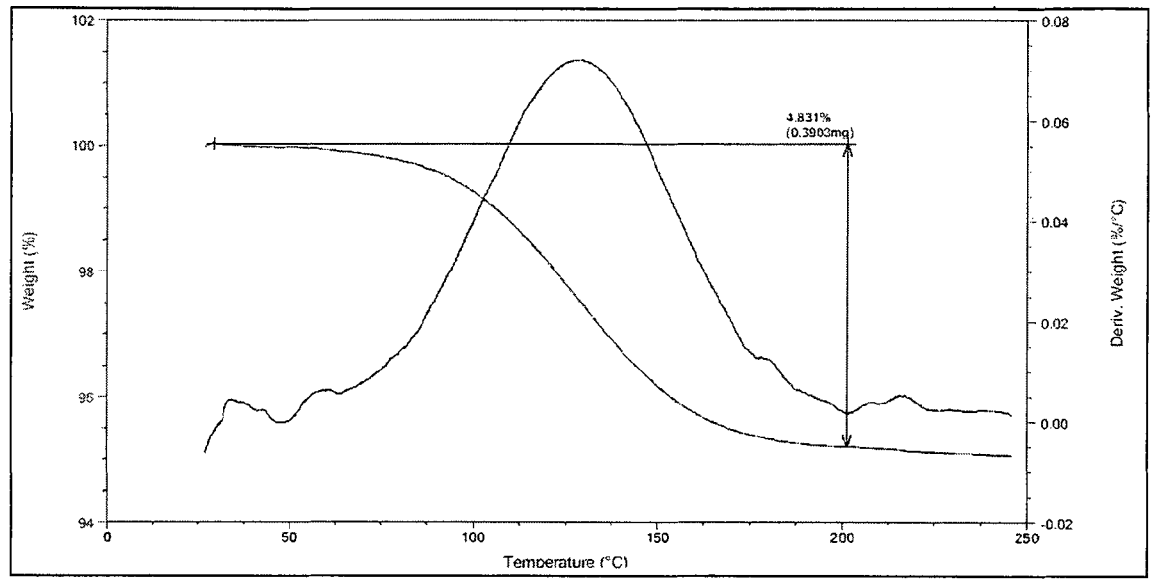
FIG. 3 shows the characteristic thermo gravimetric analysis (TGA) of ivacaftor Form-L1.

In another embodiment, the present invention provides ivacaftor Form-L1 characterized by a thermo gravimetric analysis (TGA) substantially in accordance with FIG. 3.

In another embodiment, the present invention provides a process for the preparation of ivacaftor Form-L1, comprising:
  a) suspending or mixing ivacaftor in n-heptane,
  b) heating the suspension,
  c) isolating the solid, and
  d) drying the solid at about 45° C. to about 65° C. to obtain ivacaftor Form-L1.

In the aforementioned process of ivacaftor Form-L1 includes suspending or mixing of ivacaftor or a solvate thereof, preferably diisopropyl ether solvate, propanol solvate, cyclopentyl methyl ether solvate, methyl tertiary butyl ether solvate of the present invention or a known ethanol solvate; more preferably ethanol solvate, in n-heptane at a suitable temperature, for example at about 25° C. to about 35° C. and then the suspension may be heated to about 60° C. to about reflux temperature, preferably at about 90° C. to reflux temperature. Then, isolating the ivacaftor Form-L1 from the reaction mass can be carried out by any isolation process known in the art, for example, cooling the reaction mass to a temperature of less than 35° C. followed by stirring and filtering. The wet solid obtained may be subjected to drying under vacuum at a temperature of about 45° C. to about 65° C. for sufficient period of time, preferably for 8 to 16 hours to obtain ivacaftor Form-L1.

In another embodiment, the present invention provides ivacaftor Form-L2.

Figure 4:
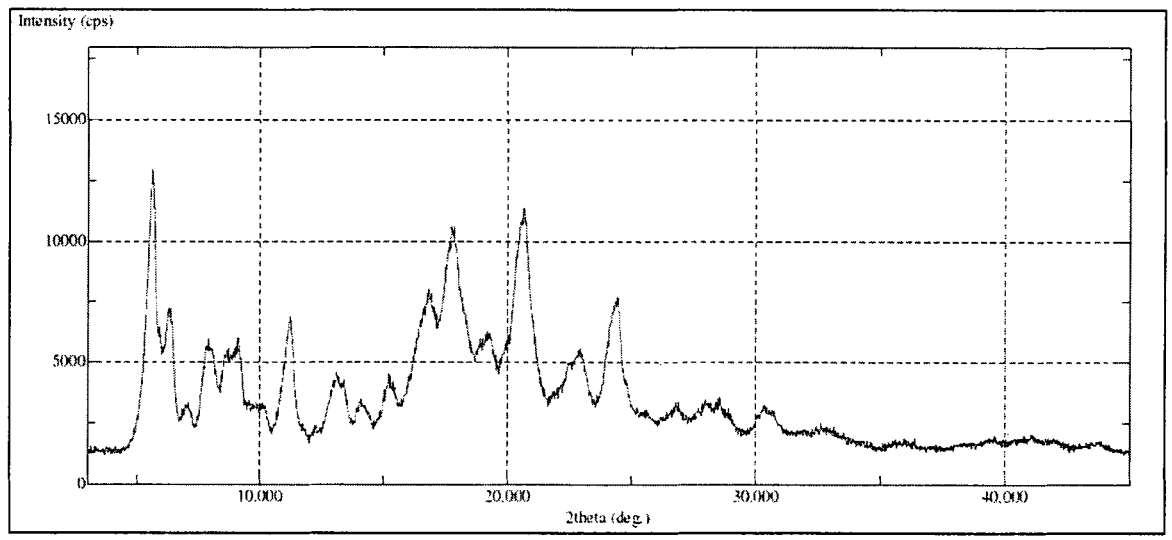
FIG. 4 shows the characteristic powder X-ray diffraction (XRD) pattern of ivacaftor Form-L2.

In another embodiment, the present invention provides ivacaftor Form-L2 characterized by a powder X-Ray diffraction (PXRD) pattern substantially in accordance with FIG. 4.

In another embodiment, the present invention provides ivacaftor Form-L2 characterized by a PXRD pattern having one or more peaks at about 5.6 5.9, 6.3, 7.0, 7.9, 8.6, 9.1, 11.2, 12.2, 13.1, 13.4, 14.1, 15.2, 16.8, 17.8, 18.9, 19.3, 20, 20.5, 20.7, 22.5, 22.9, 24.4, 26.7, 28, 28.5 and 30.3±0.2°2θ.

In another embodiment, the present invention provides ivacaftor Form-L2 characterized by a PXRD pattern having one or more peaks at about 5.6, 7.0, 13.1, 13.4, 14.1, 15.2, 16.8, 20, 20.4, 24.4 and 28.5±0.2°2θ.

Figure 5:
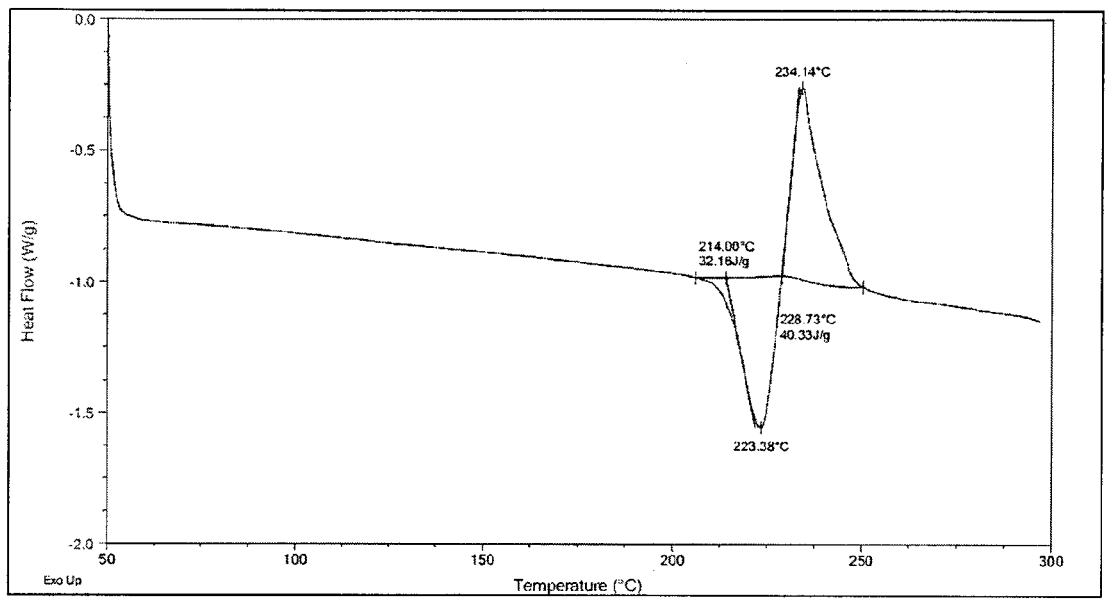
FIG. 5 shows the characteristic differential scanning calorimetric (DSC) thermogram of ivacaftor Form-L2.

In another embodiment, the present invention provides ivacaftor Form-L2 characterized by a differential scanning calorimetry (DSC) substantially in accordance with FIG. 5.

Figure 6:
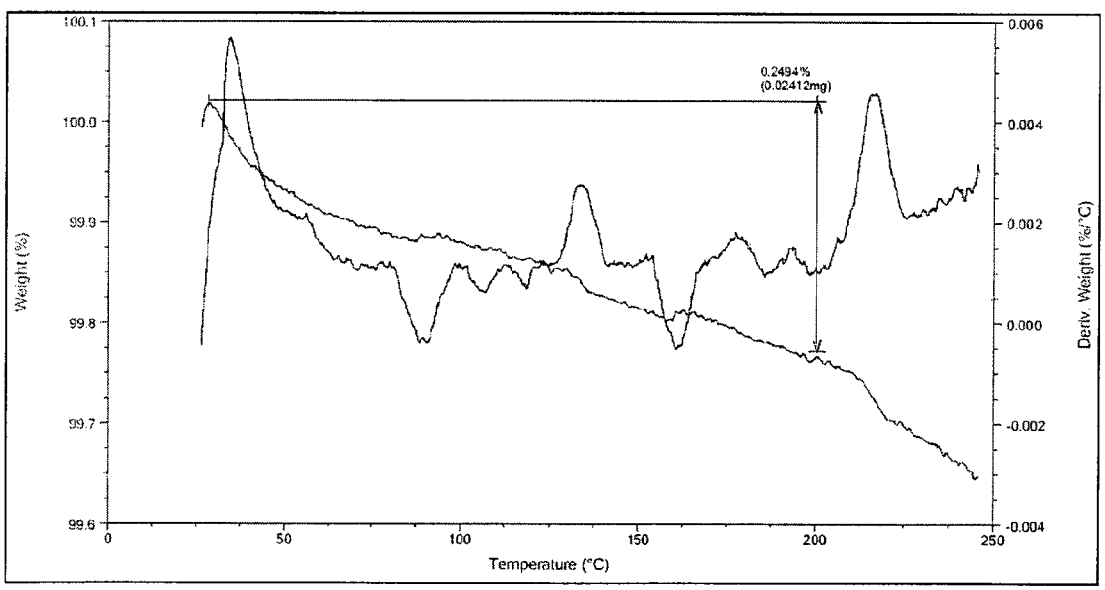
FIG. 6 shows the characteristic thermo gravimetric analysis (TGA) of ivacaftor Form-L2.

In another embodiment, the present invention provides ivacaftor Form-L2 characterized by a thermo gravimetric analysis (TGA) substantially in accordance with FIG. 6.

In another embodiment, the present invention provides a process for preparation of ivacaftor Form-L2, comprising:
  a) suspending or mixing ivacaftor or a solvate thereof in n-heptane,
  b) heating the suspension,
  c) isolating the solid; and
  d) drying the solid at about 85° C. to about 95° C. to obtain ivacaftor Form-L2.

In the aforementioned process of ivacaftor Form-L2 includes suspending or mixing ivacaftor or a solvate thereof, specifically ethanol solvate in n-heptane at a suitable temperature, for example at about 25° C. to about 35° C. and then the suspension may be heated to about 60° C. to about reflux temperature, preferably at about 90° C. to reflux temperature. Then, isolating the ivacaftor Form-L2 from the reaction mass can be carried out by any isolation process known in the art, for example, cooling the reaction mass to a temperature of less than 35° C. followed by stirring and filtering the solid. The wet solid obtained can be subjected to drying under vacuum at a temperature of about 85° C. to about 95° C. for sufficient period of time, preferably for 16 to 30 hours to obtain ivacaftor Form-L2.

In another embodiment, the present invention provides ivacaftor Form-L3.

Figure 7:
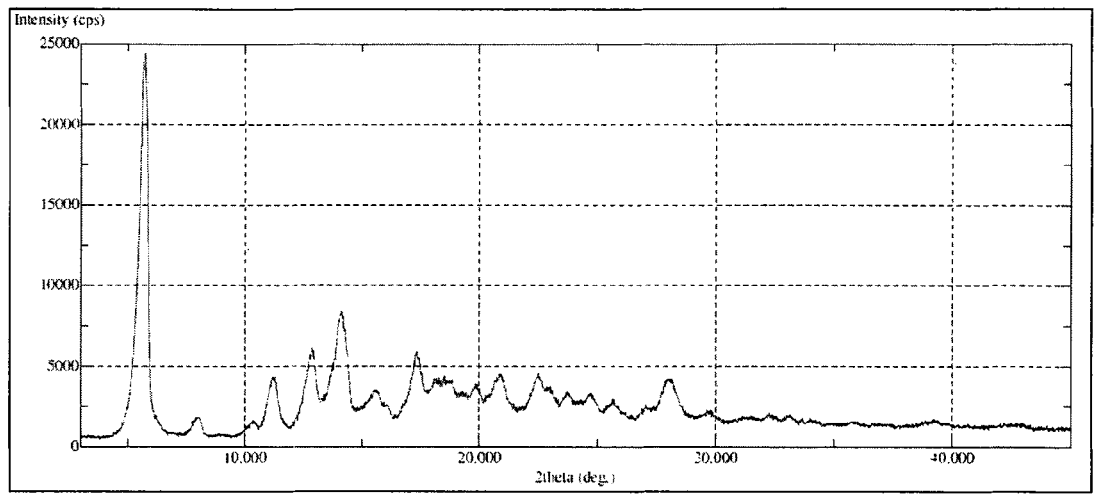
FIG. 7 shows the characteristic powder X-ray diffraction (XRD) pattern of ivacaftor Form-L3.

In another embodiment, the present invention provides ivacaftor Form-L3 characterized by a powder X-Ray diffraction (PXRD) pattern substantially in accordance with FIG. 7.

In another embodiment, the present invention provides ivacaftor Form-L3 characterized by a PXRD pattern having one or more peaks at about 5.70, 7.96, 10.36, 11.22, 12.88, 14.10, 15.60, 17.34, 18.14, 18.80, 19.84, 20.90, 22.48, 23.68, 24.64, 25.62 and 28.00±0.2°2θ.

Figure 8:
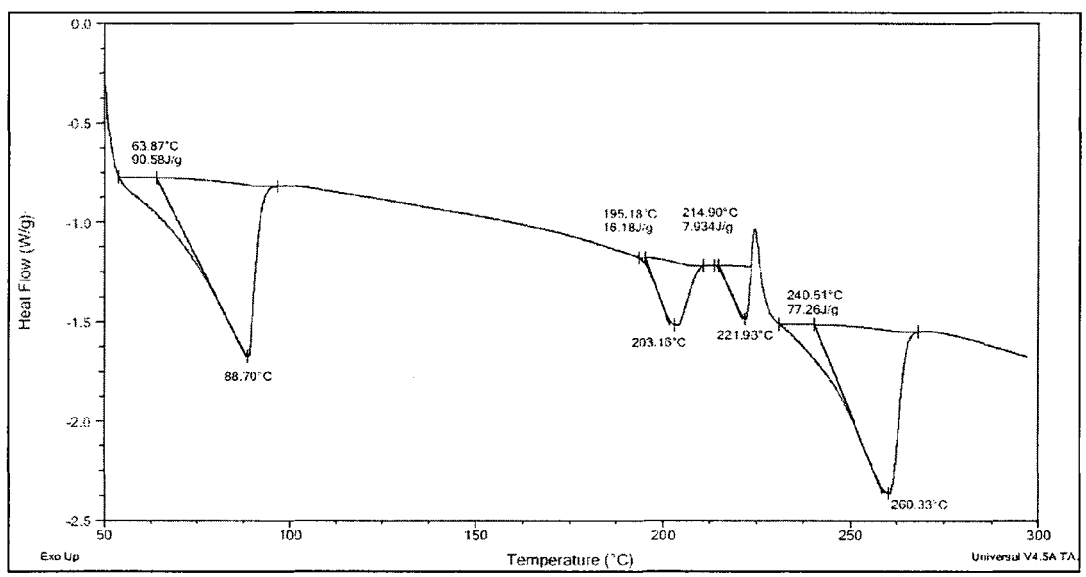
FIG. 8 shows the characteristic differential scanning calorimetric (DSC) thermogram of ivacaftor Form-L3.

In another embodiment, the present invention provides ivacaftor Form-L3 characterized by a differential scanning calorimetry (DSC) substantially in accordance with FIG. 8.

Figure 9:
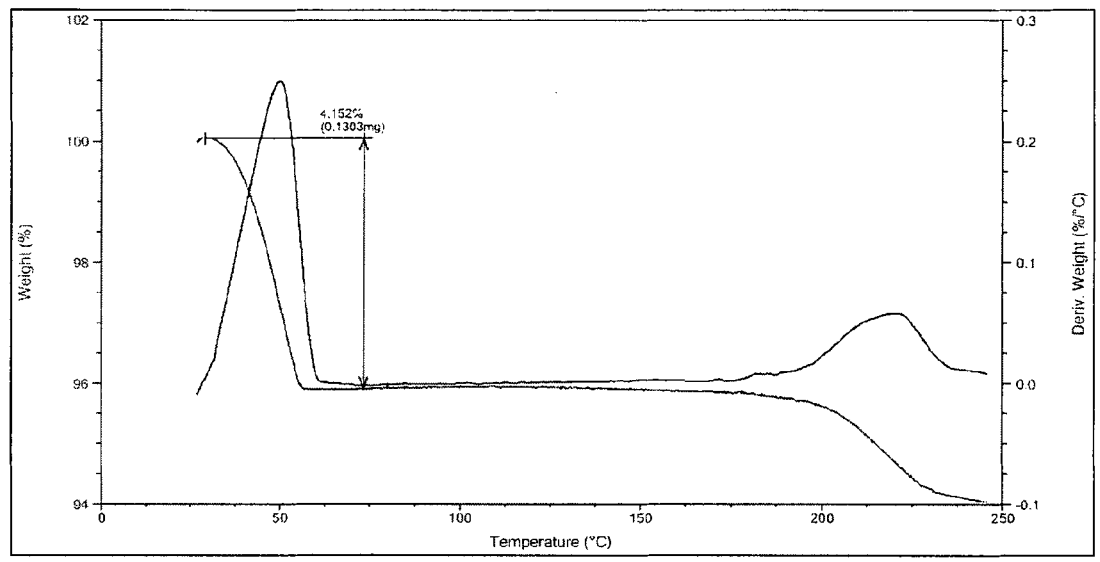
FIG. 9 shows the characteristic thermo gravimetric analysis (TGA) of ivacaftor Form-L3.

In another embodiment, the present invention provides ivacaftor Form-L3 characterized by a thermo gravimetric analysis (TGA) substantially in accordance with FIG. 9.

In another embodiment, the present invention provides a process for preparation of ivacaftor Form-L3, comprising:
   a) dissolving ivacaftor in a mixture of acetonitrile and a suitable acid at a suitable temperature,
   b) adding water to the step a) solution at about 25° C. to about 35° C.,
   c) isolating the solid; and
   d) drying the solid obtained in step c) at about 25° C. to about 35° C. to obtain ivacaftor Form-L3.

The starting ivacaftor used herein for preparing ivacaftor Form-L3 is ivacaftor ethanol solvate, which is obtained by the processes known in the art. The suitable acid used herein is selected from acetic acid, methanesulfonic acid and the like and mixtures thereof; preferably methanesulfonic acid. The suitable temperature includes from about ambient temperature to reflux temperature, preferably at about 25° C. to about 45° C. and sufficient amount of water may be added to precipitation. The resultant product may be isolated by methods known in the art, for example filtration. The wet solid obtained can be dried under vacuum at a temperature of about 25° C. to about 35° C. for sufficient period of time, preferably for about 10 to 16 hours to obtain the Form-L3.

In another embodiment, the present invention provides ivacaftor Form-L4.

Figure 10:
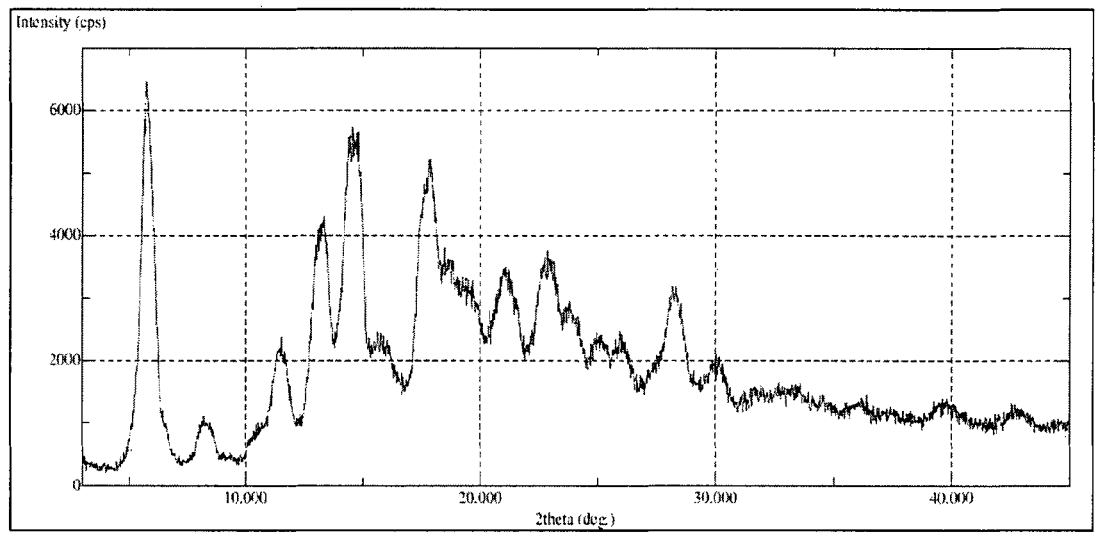
FIG. 10 shows the characteristic powder X-ray diffraction (XRD) pattern of ivacaftor Form-L4.

In another embodiment, the present invention provides ivacaftor Form-L4 characterized by a powder X-Ray diffraction (PXRD) pattern substantially in accordance with FIG. 10.

In another embodiment, the present invention provides ivacaftor Form-L4 characterized by a PXRD pattern having one or more peaks at about 5.74, 8.26, 10.68, 11.56, 13.30, 14.60, 15.76, 17.88, 21.02, 22.90, 23.78, 25.14, 25.94, 28.20 and 29.98±0.2°2θ.

Figure 11:
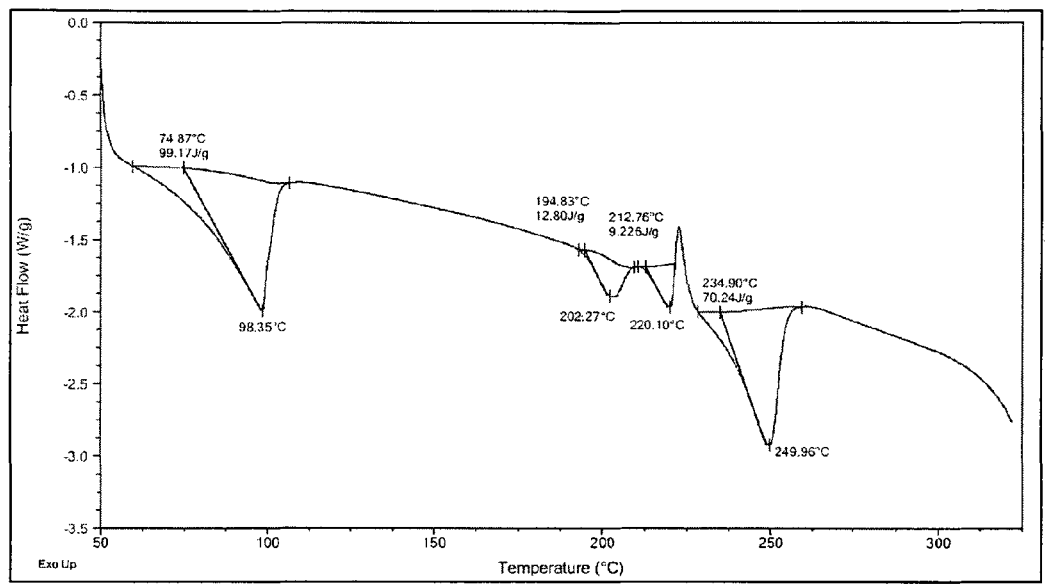
FIG. 11 shows the characteristic differential scanning calorimetric (DSC) thermogram of ivacaftor Form-L4.

In another embodiment, the present invention provides ivacaftor Form-L4 characterized by a differential scanning calorimetry (DSC) substantially in accordance with FIG. 11.

Figure 12:
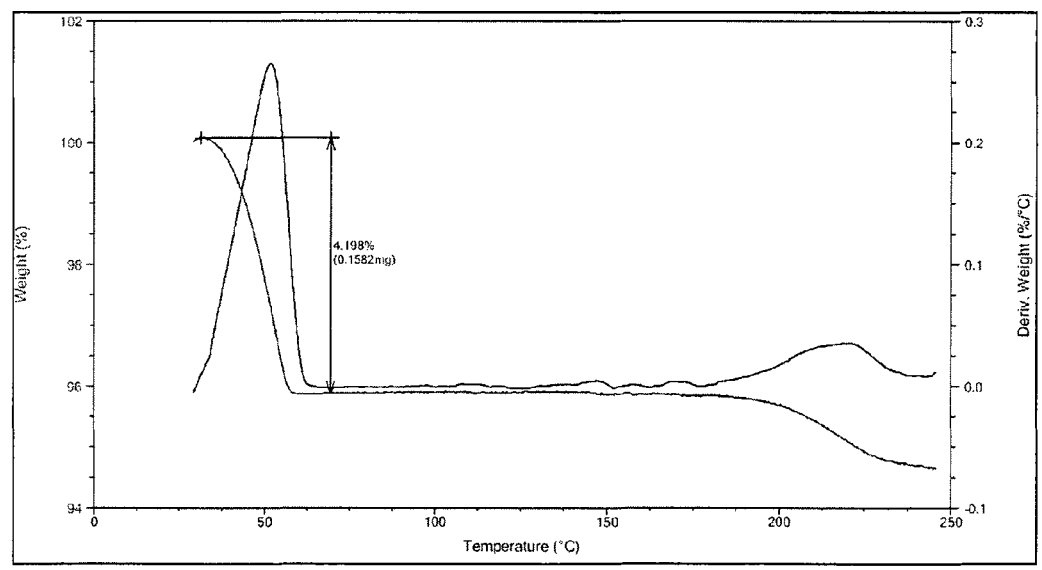
FIG. 12 shows the characteristic thermo gravimetric analysis (TGA) of ivacaftor Form-L4.

In another embodiment, the present invention provides ivacaftor Form-L4 characterized by a thermo gravimetric analysis (TGA) substantially in accordance with FIG. 12.

In another embodiment, the present invention provides a process for preparation of ivacaftor Form-L4, comprising:
   a) dissolving ivacaftor in a mixture of acetonitrile and a suitable acid at a suitable temperature,
   b) adding water to the step a) solution at about 25° C. to about 35° C.,
   c) isolating the solid; and
   d) drying the solid obtained in step c) at about 25° C. to about 35° C. to obtain ivacaftor Form-L4.

The starting ivacaftor used herein for preparing ivacaftor Form-L4 is ivacaftor ethanol solvate, which is obtained by the processes known in the art. The suitable acid used herein is selected from acetic acid, methanesulfonic acid and the like and mixtures thereof; preferably methanesulfonic acid. The suitable temperature includes from about ambient temperature to reflux temperature, preferably at about 25° C. to about 45° C. and sufficient amount of water may be added to precipitation. The resultant product may be isolated by methods known in the art, for example filtration. The wet solid obtained can be dried under vacuum at a temperature of about 25° C. to about 35° C. for sufficient period of time, preferably for about 20 to 30 hours to obtain the Form-L4.

In another embodiment, the present invention provides ivacaftor Form-L5.

Figure 13:
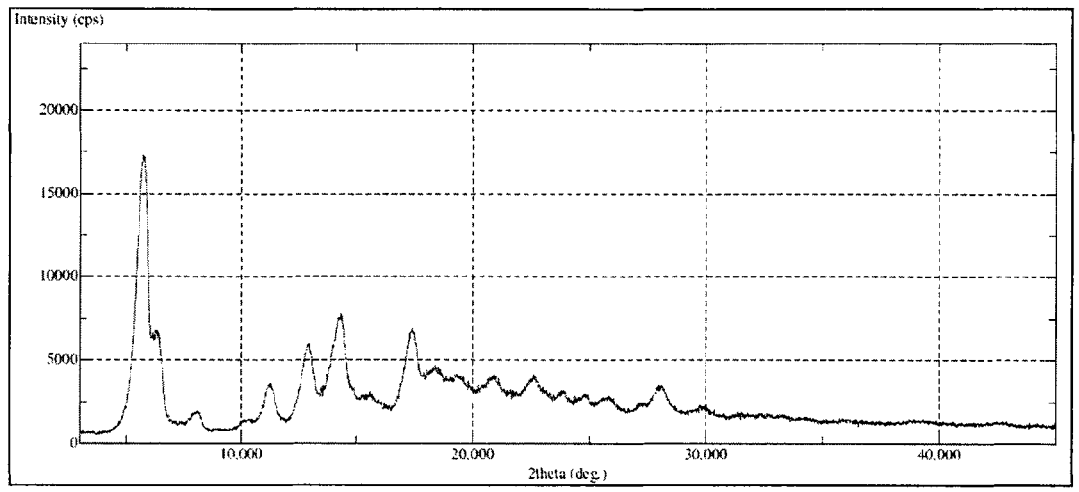
FIG. 13 shows the characteristic powder X-ray diffraction (XRD) pattern of ivacaftor Form-L5.

In another embodiment, the present invention provides ivacaftor Form-L5 characterized by a powder X-Ray diffraction (PXRD) pattern substantially in accordance with FIG. 13.

In another embodiment, the present invention provides ivacaftor Form-L5 characterized by a PXRD pattern having one or more peaks at about 5.78, 6.42, 8.08, 10.18, 11.24, 12.90, 14.02, 14.34, 15.52, 17.40, 18.38, 19.28, 20.90, 22.60, 23.84, 24.76, 25.82, 27.16, 28.00 and 29.86±0.2°2θ.

Figure 14:
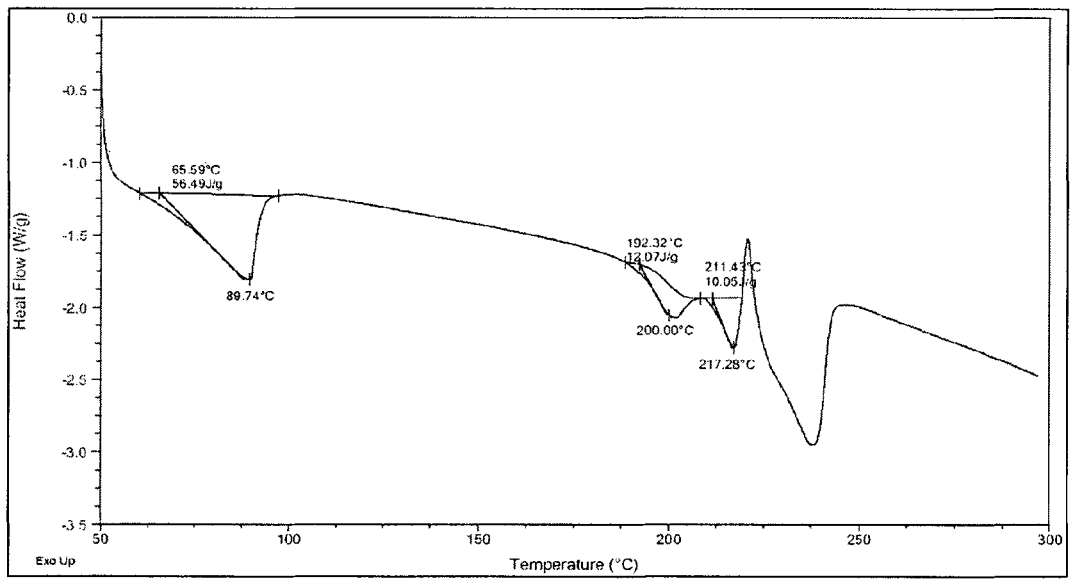
FIG. 14 shows the characteristic differential scanning calorimetric (DSC) thermogram of ivacaftor Form-L5.

In another embodiment, the present invention provides ivacaftor Form-L5 characterized by a differential scanning calorimetry (DSC) substantially in accordance with FIG. 14.

Figure 15:
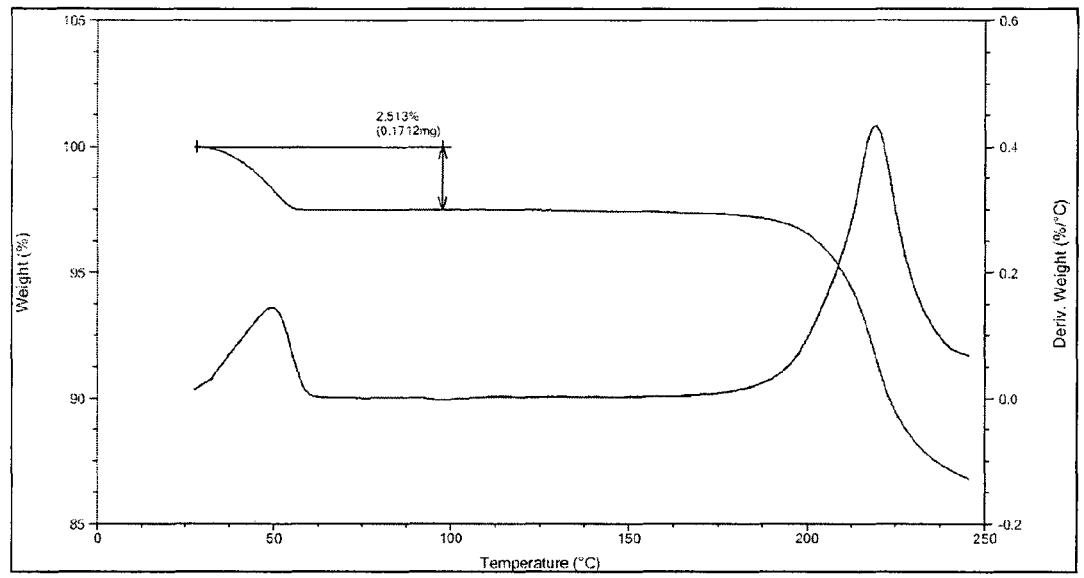
FIG. 15 shows the characteristic thermo gravimetric analysis (TGA) of ivacaftor Form-L5.

In another embodiment, the present invention provides ivacaftor Form-L5 characterized by a thermo gravimetric analysis (TGA) substantially in accordance with FIG. 15.

In another embodiment, the present invention provides a process for preparation of ivacaftor Form-L5, comprising:
   a) dissolving ivacaftor in a mixture of acetonitrile and a suitable acid at a suitable temperature,
   b) adding water to the step a) solution at about 25° C. to about 35° C.,
   c) isolating the solid; and
   d) drying the solid obtained in step c) at about 55° C. to about 65° C. to obtain ivacaftor Form-L5.

The starting ivacaftor used herein for preparing ivacaftor Form-L5 is ivacaftor ethanol solvate, which is obtained by the processes known in the art. The suitable acid used herein is selected from acetic acid, methanesulfonic acid and the like and mixtures thereof; preferably methanesulfonic acid. The suitable temperature includes from about ambient temperature to reflux temperature, preferably at about 25° C. to about 45° C. and sufficient amount of water may be added to precipitation. The resultant product may be isolated by methods known in the art, for example filtration. The wet solid obtained can be dried under vacuum at a temperature of about 55° C. to about 65° C. for sufficient period of time, preferably for about 10 to 20 hours to obtain the Form-L5.

In another embodiment, the present invention provides ivacaftor Form-L6.

Figure 16:
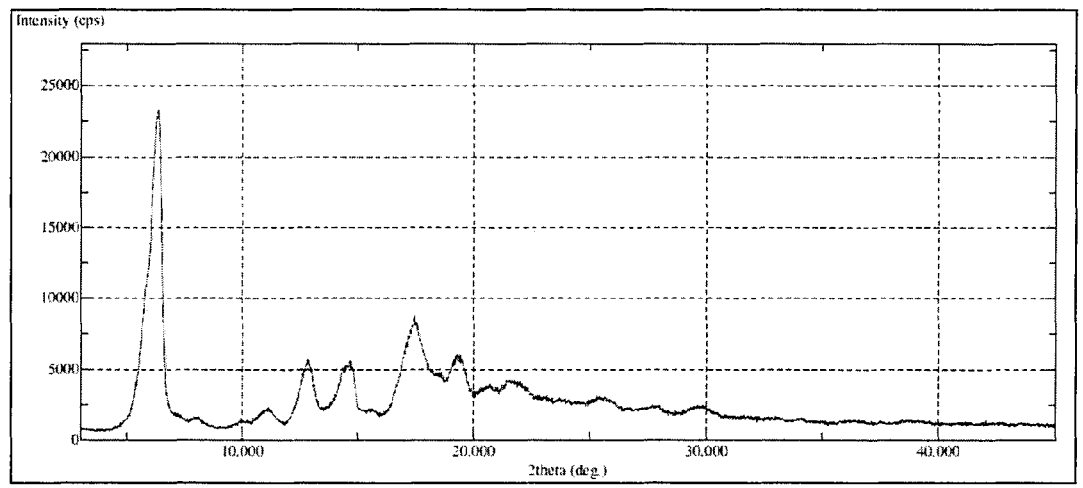
FIG. 16 shows the characteristic powder X-ray diffraction (XRD) pattern of ivacaftor Form-L6.

In another embodiment, the present invention provides ivacaftor Form-L6 characterized by a powder X-Ray diffraction (PXRD) pattern substantially in accordance with FIG. 16.

In another embodiment, the present invention provides ivacaftor Form-L6 characterized by a PXRD pattern having one or more peaks at about 6.38, 7.32, 8.10, 9.94, 11.12, 12.84, 14.64, 15.56, 17.44, 19.28, 20.66, 21.46, 25.46 and 29.62±0.2°2θ.

Figure 17:
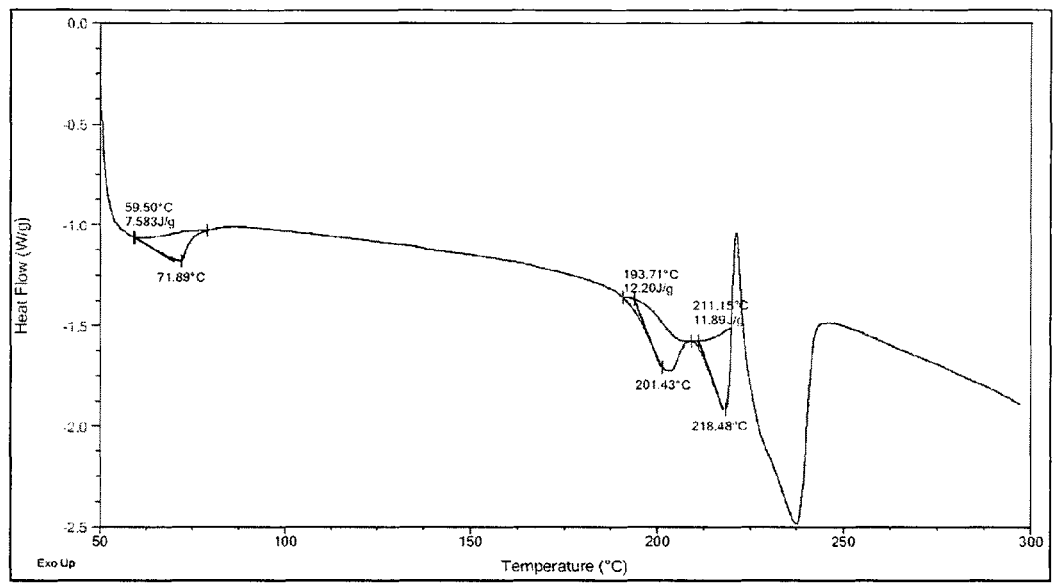
FIG. 17 shows the characteristic differential scanning calorimetric (DSC) thermogram of ivacaftor Form-L6.

In another embodiment, the present invention provides ivacaftor Form-L6 characterized by a differential scanning calorimetry (DSC) substantially in accordance with FIG. 17.

Figure 18:
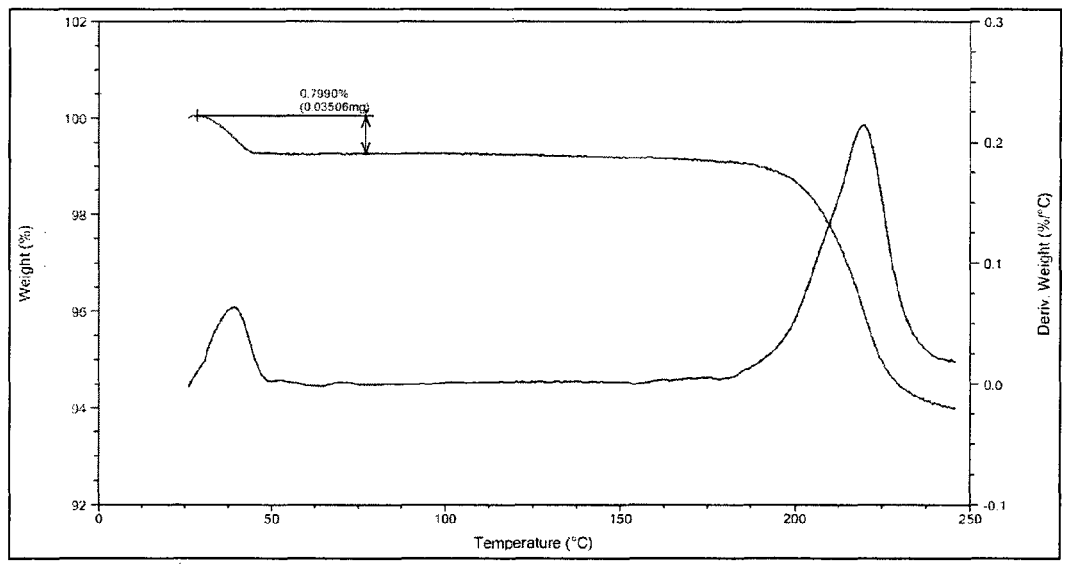
FIG. 18 shows the characteristic thermo gravimetric analysis (TGA) of ivacaftor Form-L6.

In another embodiment, the present invention provides ivacaftor Form-L6 characterized by a thermo gravimetric analysis (TGA) substantially in accordance with FIG. 18.

In another embodiment, the present invention provides a process for preparation of ivacaftor Form-L6, comprising:
   a) dissolving ivacaftor in a mixture of acetonitrile and a suitable acid at a suitable temperature,
   b) adding water to the step a) solution at 25° C. to about 35° C., c) isolating the solid; and d) drying the solid obtained in step c) at about 55° C. to about 65° C. to obtain ivacaftor Form-L6.

The starting ivacaftor used herein for preparing ivacaftor Form-L6 is ivacaftor ethanol solvate, which is obtained by the processes known in the art. The suitable acid used herein is selected from acetic acid, methanesulfonic acid and the like and mixtures thereof; preferably methanesulfonic acid. The suitable temperature includes from about ambient temperature to reflux temperature, preferably at about 25° C. to about 45° C. and sufficient amount of water may be added to precipitation. The resultant product may be isolated by methods known in the art, for example filtration. The wet solid obtained can be dried under vacuum at a temperature of about 55° C. to about 65° C. for sufficient period of time, preferably for about 20 to 30 hours to obtain the Form-L6.

In another embodiment, the present invention provides ivacaftor Form-L7.

Figure 19:
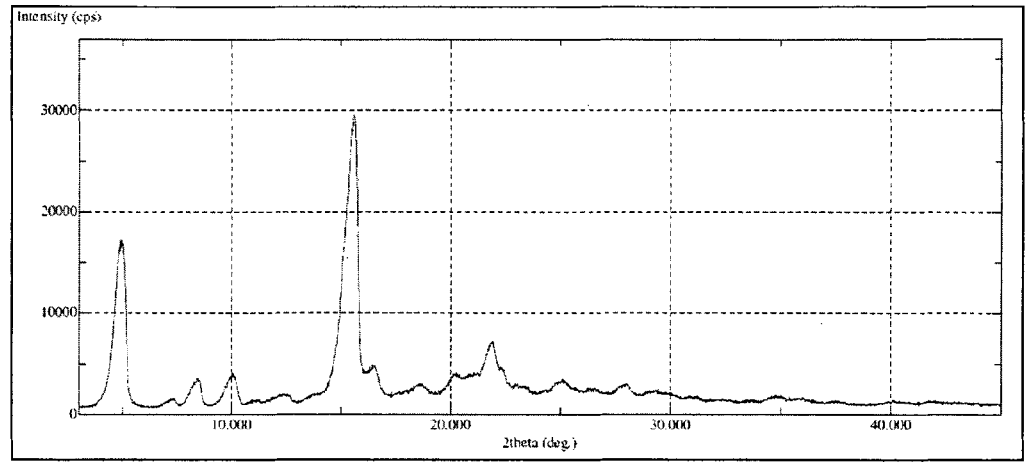
FIG. 19 shows the characteristic powder X-ray diffraction (XRD) pattern of ivacaftor Form-L7.

In another embodiment, the present invention provides ivacaftor Form-L7 characterized by a powder X-Ray diffraction (PXRD) pattern substantially in accordance with FIG. 19.

In another embodiment, the present invention provides ivacaftor Form-L7 characterized by a PXRD pattern having one or more peaks at about 5.0, 7.32, 8.46, 10.08, 12.38, 13.66, 15.62, 16.54, 18.58, 20.18, 21.88, 22.36, 23.00, 24.30, 24.80, 25.12, 25.64, 26.30, 26.54, 27.60, 28.06 and 29.30±0.2°2θ.

Figure 20:
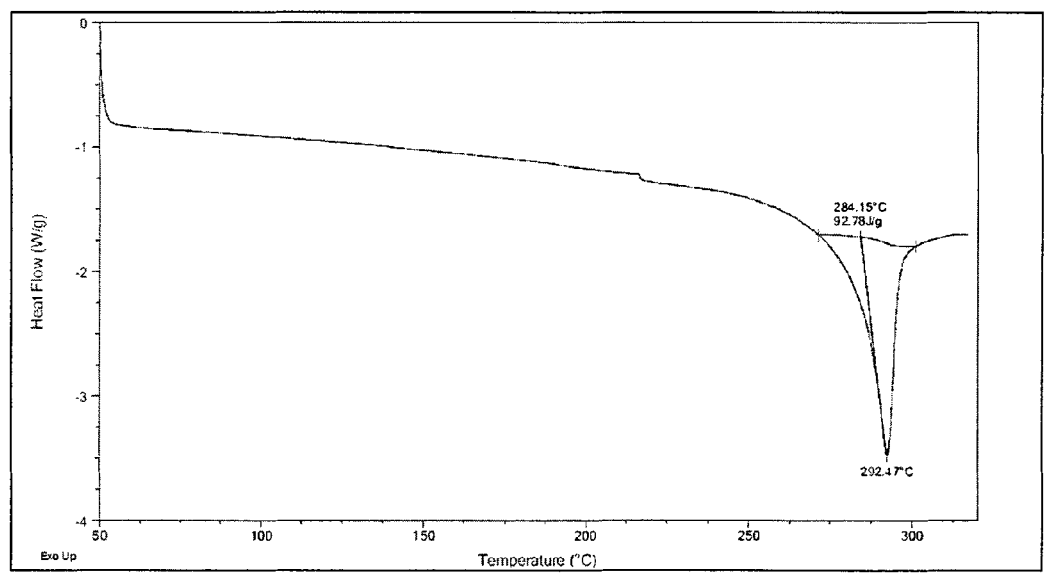
FIG. 20 shows the characteristic differential scanning calorimetric (DSC) thermogram of ivacaftor Form-L7.

In another embodiment, the present invention provides ivacaftor Form-L7 characterized by a differential scanning calorimetry (DSC) substantially in accordance with FIG. 20.

Figure 21:
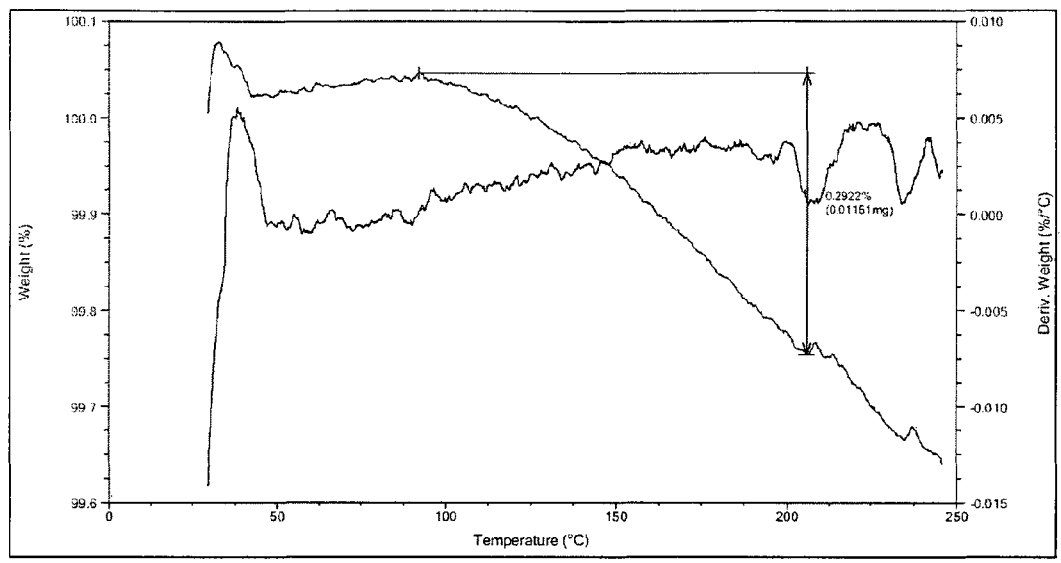
FIG. 21 shows the characteristic thermo gravimetric analysis (TGA) of ivacaftor Form-L7.

In another embodiment, the present invention provides ivacaftor Form-L7 characterized by a thermo gravimetric analysis (TGA) substantially in accordance with FIG. 21.

In another embodiment, the present invention provides a process for preparation of ivacaftor Form-L7, comprising:

a) dissolving ivacaftor in a mixture of acetonitrile and a suitable acid at a suitable temperature, b) adding water to the step a) solution at 25° C. to about 35° C., c) isolating the solid; and d) drying the solid obtained in step c) at about 75° C. to about 100° C. to obtain ivacaftor Form-L7.

The starting ivacaftor used herein for preparing ivacaftor Form-L7 is ivacaftor, ethanol solvate, which is obtained by the processes known in the art. The suitable acid used herein is selected from acetic acid, methanesulfonic acid and the like and mixtures thereof; preferably methanesulfonic acid. The suitable temperature includes from about ambient temperature to reflux temperature, preferably at about 25° C. to about 45° C. and sufficient amount of water may be added to precipitation. The resultant product may be isolated by methods known in the art, for example filtration. The wet solid obtained can be dried under vacuum at a temperature of about 75° C. to about 100° C. for sufficient period of time, preferably for about 5 to 10 hours to obtain the Form-L7.

In another embodiment, the present invention provides ivacaftor Form-L8.

In another embodiment, the ivacaftor Form-L8 of the present invention is a cyclohexane solvate.

Figure 22:
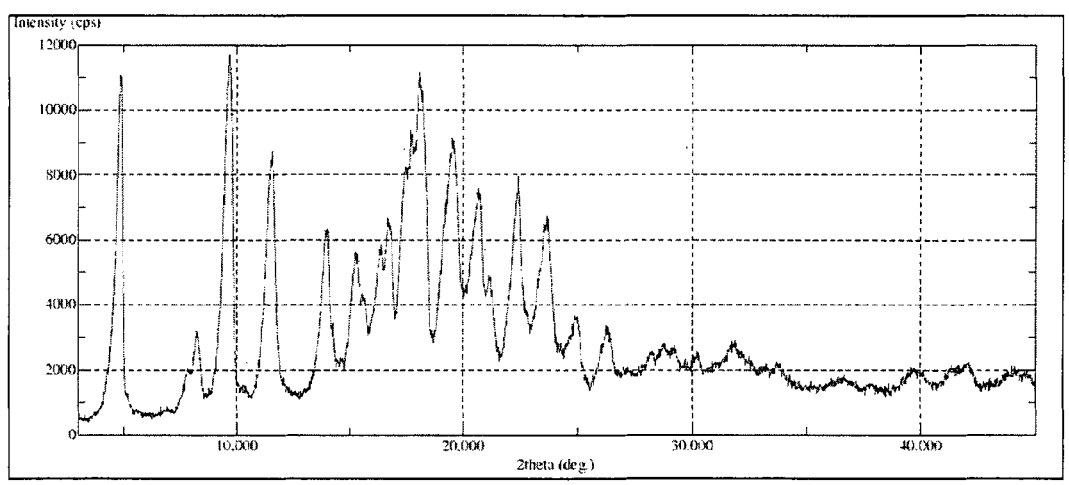
FIG. 22 shows the characteristic powder. X-ray diffraction (XRD) pattern of ivacaftor Form-L8.

In another embodiment, the present invention provides ivacaftor Form-L8 characterized by a powder X-Ray diffraction (PXRD) pattern substantially in accordance with FIG. 22.

In another embodiment, the present invention provides ivacaftor Form-L8 characterized by a PXRD pattern having one or more peaks at about 4.86, 7.84, 8.24, 9.70, 11.56, 13.98, 15.26, 15.62, 16.34, 16.70, 17.40, 17.70, 18.10, 19.60, 20.72, 21.16, 22.40, 23.66, 24.96, 26.30, 28.72, 30.14 and 31.76±0.2°2θ.

Figure 23:
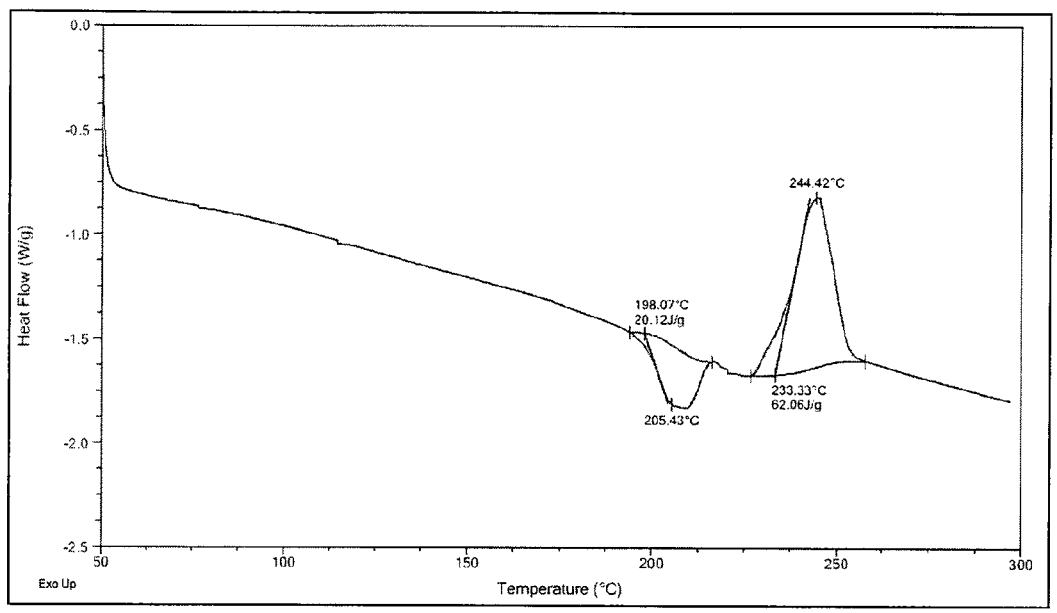
FIG. 23 shows the characteristic differential scanning calorimetric (DSC) thermogram of ivacaftor Form-L8.

In another embodiment, the present invention provides ivacaftor Form-L8 characterized by a differential scanning calorimetry (DSC) substantially in accordance with FIG. 23.

Figure 24:
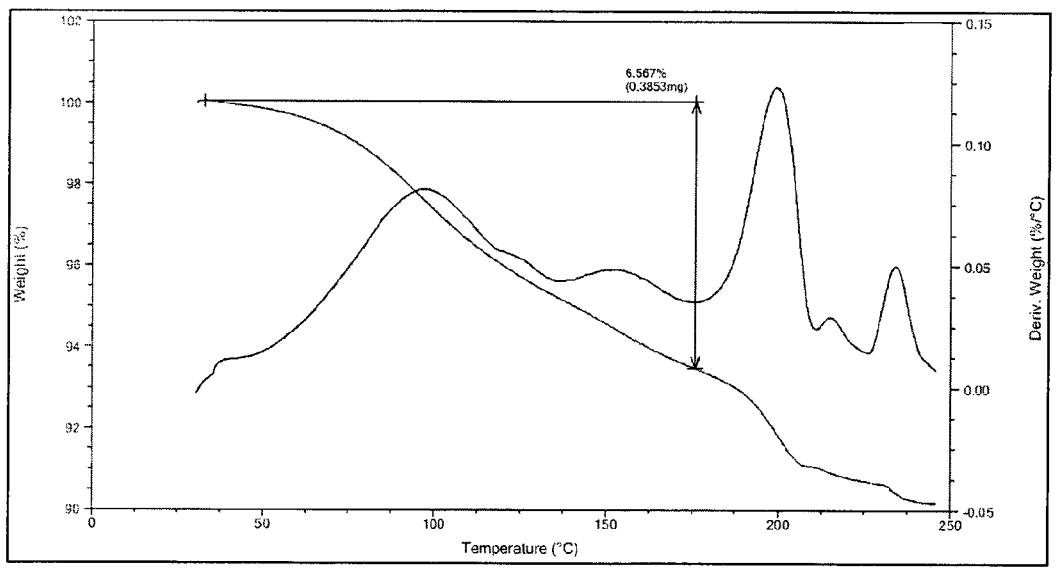
FIG. 24 shows the characteristic thermo gravimetric analysis (TGA) of ivacaftor Form-L8.

In another embodiment, the present invention provides ivacaftor Form-L8 characterized by a thermo gravimetric analysis (TGA) substantially in accordance with FIG. 24.

In another embodiment, the present invention provides a process for the preparation of ivacaftor Form-L8, comprising:

a) suspending or mixing ivacaftor in cyclohexane, b) heating the suspension, c) isolating the solid; and d) drying the solid to obtain ivacaftor Form-L8.

In the aforementioned process of ivacaftor Form-L8 includes suspending or mixing ivacaftor or a solvate thereof, preferably ethanol solvate or ivacaftor monohydrate obtained by the processes known in the art, in cyclohexane at a suitable temperature, for example at about 25° C. to about 35° C. and then the suspension may be heated to about 65° C. to about reflux temperature, preferably at about 75° C. to about 85° C. Then, isolating the ivacaftor Form-L8 from the reaction mass can be carried out by any isolation process known in the art, for example, cooling the reaction mass to a temperature of less than 35° C. followed by stirring and filtering. The wet solid obtained may be subjected to drying under vacuum at a temperature of about 40° C. to about 50° C. for sufficient period of time, preferably for 2 to 8 hours to obtain ivacaftor Form-L8.

In another embodiment, the present invention provides ivacaftor Form-L9.

In another embodiment, the ivacaftor Form-L9 of the present invention is a diisopropylether (DIPE) solvate.

Figure 25:
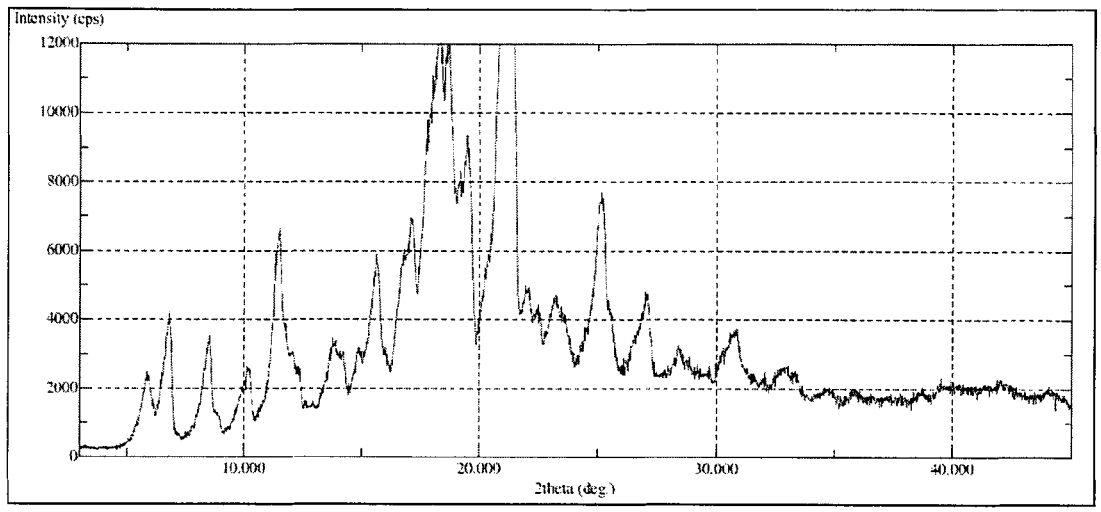
FIG. 25 shows the characteristic powder X-ray diffraction (XRD) pattern of ivacaftor Form-L9.

In another embodiment, the present invention provides ivacaftor Form-L9 characterized by a powder X-Ray diffraction (PXRD) pattern substantially in accordance with FIG. 25.

In another embodiment, the present invention provides ivacaftor Form-L9 characterized by a PXRD pattern having one or more peaks at about 5.86, 6.84, 8.50, 10.18, 11.48, 11.96, 13.82, 14.84, 15.66, 16.74, 17.12, 18.28, 18.66, 19.50, 21.02, 21.30, 22.06, 22.42, 23.20, 25.16, 25.50, 27.02, 28.44, 30.74 and 32.84±0.2°2θ.

In another embodiment, the present invention provides a process for the preparation of ivacaftor Form-L9, comprising:

a) suspending or mixing ivacaftor in diisopropylether, b) heating the suspension, c) isolating the solid; and d) drying the solid to obtain ivacaftor Form-L9.

In the aforementioned process of ivacaftor Form-L9 includes suspending or mixing ivacaftor or a solvate thereof, preferably ethanol solvate or ivacaftor monohydrate obtained by the processes known in the art, in diisopropylether at a suitable temperature, for example at about 25° C. to about 35° C. and then the suspension may be heated to about 55° C. to about reflux temperature, preferably at about 60° C. to about 70° C. Then, isolating the ivacaftor Form-L9 from the reaction mass can be carried out by any isolation process known in the art, for example, cooling the reaction mass to a temperature of less than 35° C. followed by stirring and filtering. The wet solid obtained may be subjected to drying under vacuum at a temperature of about 25° C. to about 50° C. for sufficient period of time, preferably for 4 to 16 hours to obtain ivacaftor Form-L9.

In another embodiment, the present invention provides ivacaftor Form-L10.

In another embodiment, the ivacaftor Form-L10 of the present invention is an n-propanol solvate.

Figure 26:
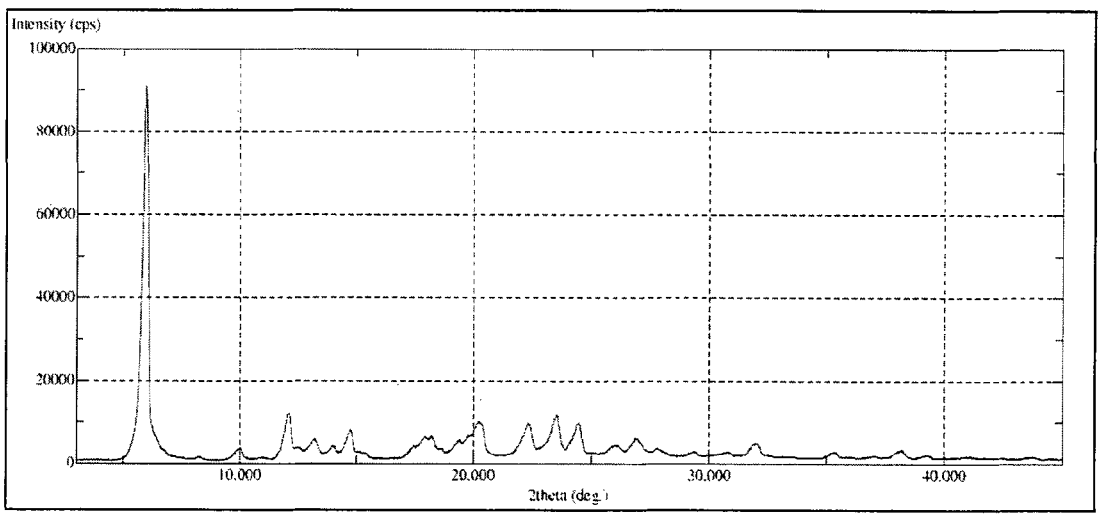
FIG. 26 shows the characteristic powder X-ray diffraction (XRD) pattern of ivacaftor Form-L10.

In another embodiment, the present invention provides ivacaftor Form-L10 characterized by a powder X-Ray diffraction (PXRD) pattern substantially in accordance with FIG. 26.

In another embodiment, the present invention provides ivacaftor Form-L10 characterized by a PXRD pattern having one or more peaks at about 5.98, 8.26, 9.94, 10.92, 12.10, 12.54, 13.24, 13.98, 14.74, 15.36, 17.42, 17.96, 18.24, 18.66, 19.38, 19.80, 20.24, 22.38, 23.54, 24.46, 25.98, 26.86, 27.76, 29.30, 30.74, 32.02, 35.30 and 38.22±0.2°2θ.

In another embodiment, the present invention provides a process for the preparation of ivacaftor Form-L10, comprising:
a) suspending or mixing ivacaftor in n-propanol,
b) heating the suspension,
c) isolating the solid; and
d) drying the solid to obtain ivacaftor Form-L10.

In the aforementioned process of ivacaftor Form-L10 includes suspending or mixing ivacaftor or a solvate thereof, preferably ethanol solvate or ivacaftor monohydrate obtained by the processes known in the art, in n-propanol at a suitable temperature, for example at about 25° C. to about 35° C. and then the suspension may be heated to about 60° C. to about reflux temperature, preferably at about 90° C. to reflux temperature. Then, isolating the ivacaftor Form-L10 from the reaction mass can be carried out by any isolation process known in the art, for example, cooling the reaction mass to a temperature of less than 35° C. followed by stirring and filtering. The wet solid obtained may be subjected to drying under vacuum at a temperature of about 40° C. to about 65° C. for sufficient period of time, preferably for 4 to 16 hours to obtain ivacaftor Form-L10.

In another embodiment, the present invention provides ivacaftor Form-L11.

In another embodiment, the ivacaftor Form-L11 of the present invention is methyl tertiary butyl ether solvate.

Figure 27:
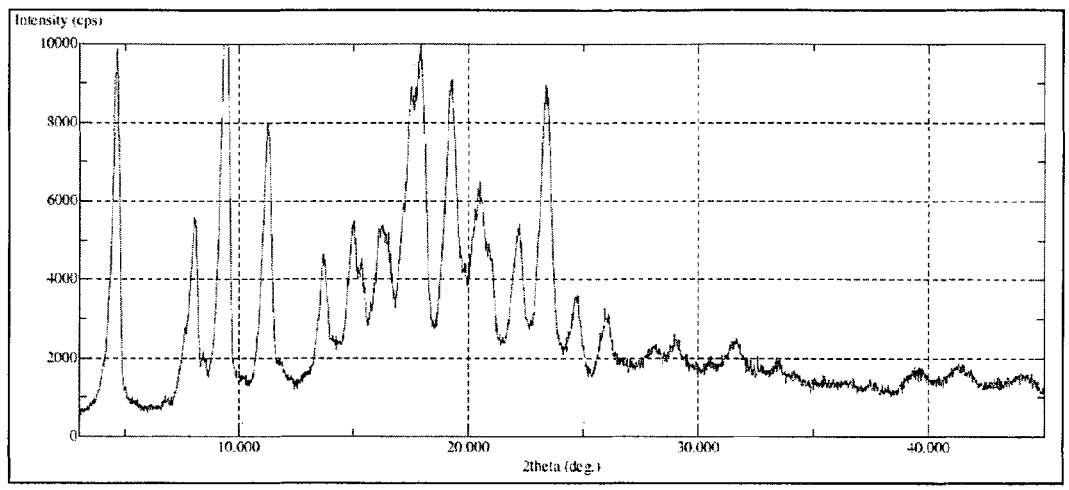
FIG. 27 shows the characteristic powder X-ray diffraction (XRD) pattern of ivacaftor Form-L11.

In another embodiment, the present invention provides ivacaftor Form-L11 characterized by a powder X-Ray diffraction (PXRD) pattern substantially in accordance with FIG. 27.

In another embodiment, the present invention provides ivacaftor Form-L11 characterized by a PXRD pattern having one or more peaks at about 4.66, 8.08, 8.46, 9.46, 11.30, 13.70, 14.98, 15.36, 16.26, 17.50, 17.90, 19.24, 20.44, 20.86, 22.16, 23.38, 24.64, 25.94, 29.04 and 31.60±0.2°2θ.

In another embodiment, the present invention provides a process for the preparation of ivacaftor Form-L11, comprising:
a) suspending or mixing ivacaftor in methyl tertiary butyl ether,
b) heating the suspension,
c) isolating the solid; and
d) drying the solid to obtain ivacaftor Form-L11.

In the aforementioned process of ivacaftor Form-L11 includes suspending or mixing ivacaftor or a solvate thereof, preferably ethanol solvate, which is obtained by the processes known in the art, in methyl tertiary butyl ether at a suitable temperature, for example at about 25° C. to about 35° C. and then the suspension may be heated to about 40° C. to about reflux temperature, preferably at about 45° C. to about reflux temperature. Then, isolating the ivacaftor Form-L11 from the reaction mass can be carried out by any isolation process known in the art, for example, cooling the reaction mass to a temperature of less than 35° C. followed by stirring and filtering. The wet solid obtained may be subjected to drying under vacuum at a temperature of about 25° C. to about 95° C. for sufficient period of time, preferably for 3 to 26 hours to obtain ivacaftor Form-L11.

In another embodiment, the present invention provides ivacaftor Form-L12A.

In another embodiment, the ivacaftor Form-L12A of the present invention is cyclopentyl methyl ether solvate.

Figure 28:
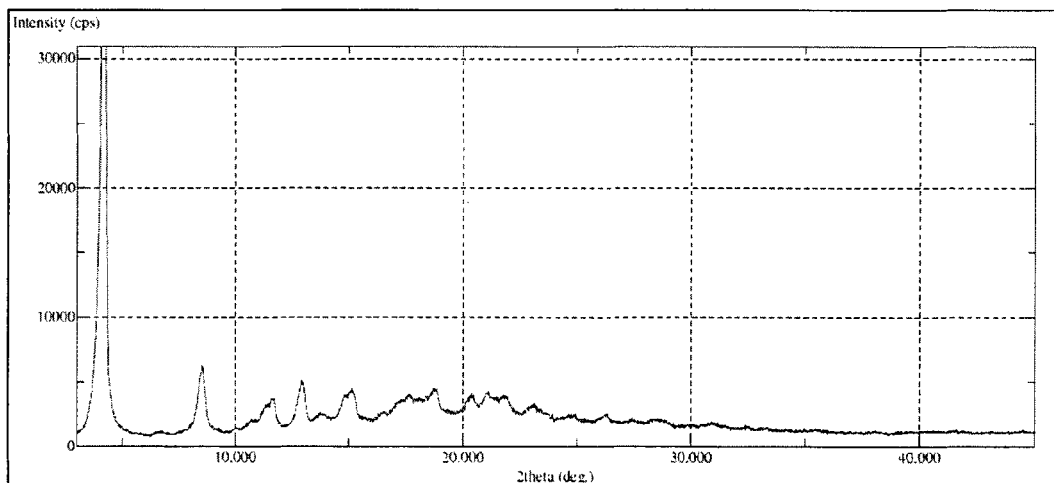
FIG. 28 shows the characteristic powder X-ray diffraction (XRD) pattern of ivacaftor Form-L12A.

In another embodiment, the present invention provides ivacaftor Form-L12A characterized by a powder X-Ray diffraction (PXRD) pattern substantially in accordance with FIG. 28.

In another embodiment, the present invention provides ivacaftor Form-L12A characterized by a PXRD pattern having one or more peaks at about 4.18, 8.56, 11.32, 11.68, 12.96, 15.04, 15.18, 17.62, 18.76, 20.28, 21.06, 23.00 and 26.22±0.2°2θ.

In another embodiment, the present invention provides a process for the preparation of ivacaftor Form-L12A, comprising:
a) suspending or mixing ivacaftor in cyclopentyl methyl ether,
b) heating the suspension,
c) isolating the solid; and
d) drying the solid at about 40° C. to about 50° C. to obtain ivacaftor Form-L12A.

In the aforementioned process of ivacaftor Form-L12A includes suspending or mixing ivacaftor or a solvate, preferably ethanol solvate, which is obtained by the processes known in the art, in cyclopentyl methyl ether at a suitable temperature, for example at about 25° C. to about 35° C. and then the suspension may be heated to about 65° C. to about reflux temperature, preferably at about 90° C. to about reflux temperature. Then, isolating the ivacaftor Form-L12A from the reaction mass can be carried out by any isolation process known in the art, for example, cooling the reaction mass to a temperature of less than 35° C. followed by stirring and filtering. The wet solid obtained may be subjected to drying under vacuum at a temperature of about 35° C. to about 50° C. for sufficient period of time, preferably for 3 to 7 hours to obtain ivacaftor Form-L12A.

In another embodiment, the present invention provides ivacaftor Form-L12B.

In another embodiment, the ivacaftor Form-L12B of the present invention is cyclopentyl methyl ether solvate.

Figure 29:
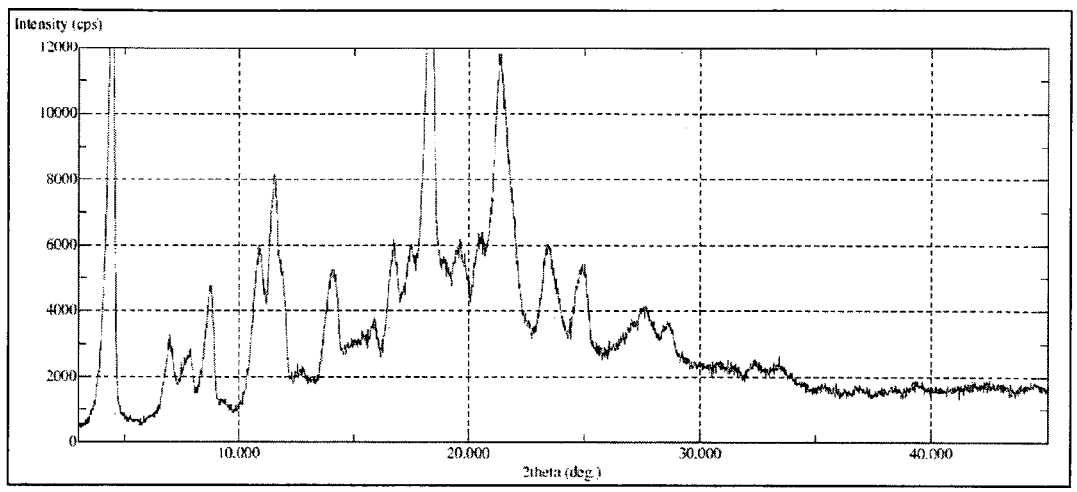
FIG. 29 shows the characteristic powder X-ray diffraction (XRD) pattern of ivacaftor Form-L12B.

In another embodiment, the present invention provides ivacaftor Form-L12B characterized by a powder X-Ray diffraction (PXRD) pattern substantially in accordance with FIG. 29.

In another embodiment, the present invention provides ivacaftor Form-L12B characterized by a PXRD pattern having one or more peaks at about 4.46, 6.96, 7.88, 8.78, 10.88, 11.52, 11.80, 14.16, 15.84, 16.72, 17.50, 18.30, 18.88, 19.64, 20.52, 21.32, 23.46, 24.88, 27.52 and 28.64±0.2°2θ.

In another embodiment, the present invention provides a process for the preparation of ivacaftor Form-L12B, comprising:
a) suspending or mixing ivacaftor in cyclopentyl methyl ether,
b) heating the suspension,
c) isolating the solid; and
d) drying the solid at about 25° C. to about 35° C. to obtain ivacaftor Form-L12B.

In the aforementioned process of ivacaftor Form-L12B includes suspending or mixing ivacaftor or a solvate thereof, preferably ethanol solvate, which is obtained by the processes known in the art in cyclopentyl methyl ether at a suitable temperature, for example at about 25° C. to about 35° C. and then the suspension may be heated to about 65° C. to about reflux temperature, preferably about 90° C. to about reflux temperature. Then, isolating the ivacaftor Form-L12B from the reaction mass can be carried out by any isolation process known in the art, for example, cooling the reaction mass to a temperature of less than 35° C. followed by stirring and filtering. The wet solid obtained may be subjected to drying under vacuum at a temperature of about 20° C. to about 35° C. for sufficient period of time, preferably for 4 to 16 hours to obtain ivacaftor Form-L12B.

In another embodiment, the present invention provides ivacaftor Form-L13.

In another embodiment, the ivacaftor Form-L13 of the present invention is n-hexane solvate.

Figure 30:
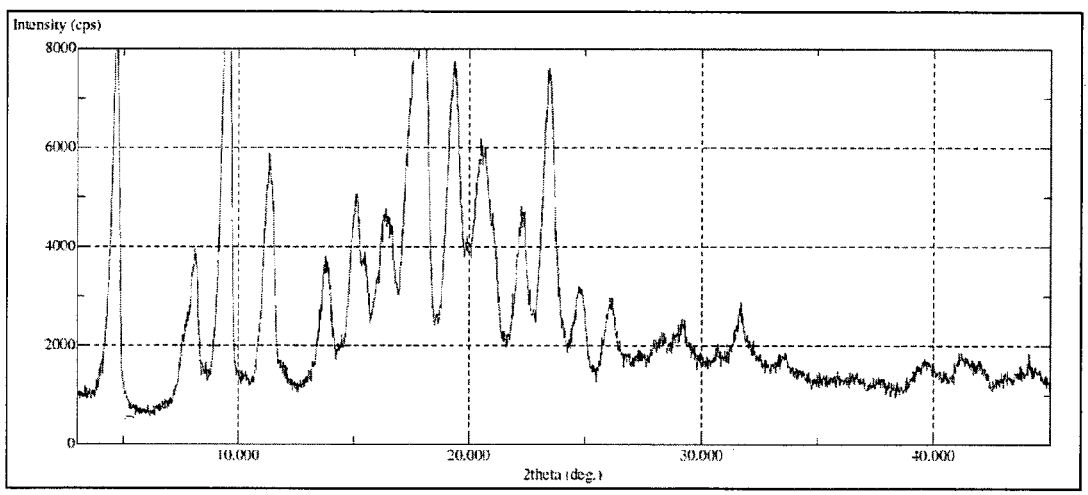
FIG. 30 shows the characteristic powder X-ray diffraction (XRD) pattern of ivacaftor Form-L13.

In another embodiment, the present invention provides ivacaftor Form-L13 characterized by a powder X-Ray diffraction (PXRD) pattern substantially in accordance with FIG. 30.

In another embodiment, the present invention provides ivacaftor Form-L13 characterized by a PXRD pattern having one or more peaks at about 4.72, 8.16, 9.50, 11.38, 13.78, 15.10, 15.46, 16.36, 17.70, 17.94, 19.36, 20.52, 22.32, 23.46, 24.72, 26.10, 29.16 and 31.64±0.2°2θ.

In another embodiment, the present invention provides a process for the preparation of ivacaftor Form-L13, comprising:
  a) suspending or mixing ivacaftor in n-hexane,
  b) heating the suspension,
  c) isolating the solid; and
  d) drying the solid at about 25° C. to about 35° C. to obtain ivacaftor Form-L13.

In the aforementioned process of ivacaftor Form-L13 includes suspending or mixing ivacaftor or a solvate thereof, preferably ethanol solvate, which is obtained by the processes known in the art, in n-hexane at a suitable temperature, for example at about 25° C. to about 35° C. and then the suspension may be heated to about 45° C. to about reflux temperature, preferably about 55° C. to about reflux temperature. Then, isolating the ivacaftor Form-L13 from the reaction mass can be carried out by any isolation process known in the art, for example, cooling the reaction mass to a temperature of less than 35° C. followed by stirring and filtering. The wet solid obtained may be subjected to drying under vacuum at a temperature of about 25° C. to about 35° C. for sufficient period of time, preferably for 20 to 28 hours to obtain ivacaftor Form-L13.

In another embodiment, the present invention provides ivacaftor Form-L14.

Figure 31:
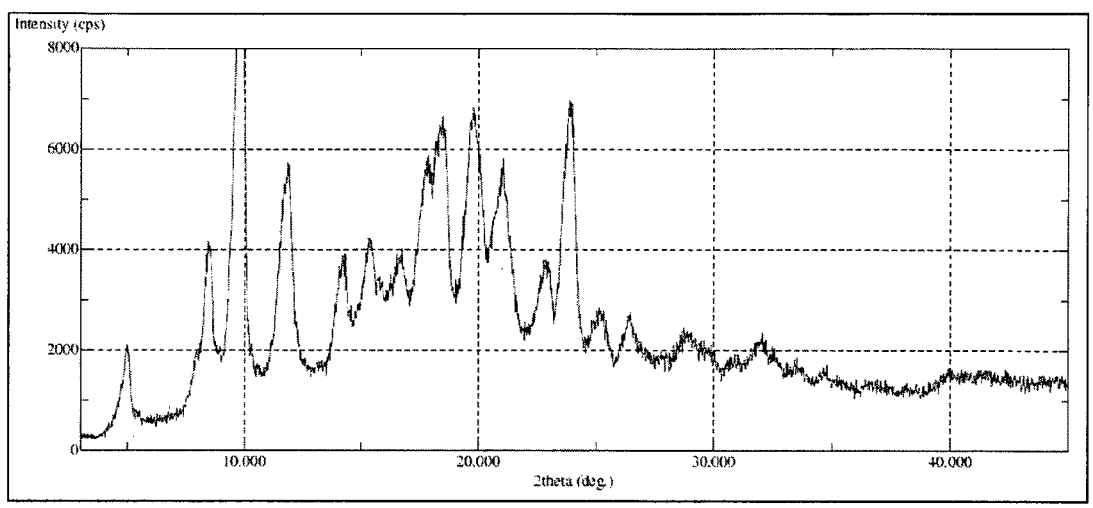
FIG. 31 shows the characteristic powder X-ray diffraction (XRD) pattern of ivacaftor Form-L14.

In another embodiment, the present invention provides ivacaftor Form-L14 characterized by a powder X-Ray diffraction (PXRD) pattern substantially in accordance with FIG. 31.

In another embodiment, the present invention provides ivacaftor Form-L14 characterized by a PXRD pattern having one or more peaks at about 4.98, 8.04, 8.50, 9.82, 11.84, 14.18, 15.38, 16.64, 17.74, 18.42, 19.72, 21.00, 22.82, 23.84, 25.14, 26.38, 28.88, 32.04±0.2°2θ.

In another embodiment, the present invention provides a process for the preparation of ivacaftor Form-L14, comprising:
  a) suspending or mixing ivacaftor in n-hexane,
  b) heating the suspension,
  c) isolating the solid; and
  d) drying the solid at about 85° C. to about 95° C. to obtain ivacaftor Form-L14.

In the aforementioned process of ivacaftor Form-L14 includes suspending or mixing ivacaftor or a solvate thereof, preferably ethanol solvate, which is obtained by the processes known in the art, in n-hexane at a suitable temperature, for example at about 25° C. to about 35° C. and then the suspension may be heated to about 45° C. to about reflux temperature, preferably at about 55° C. to about reflux temperature. Then, isolating the ivacaftor Form-L14 from the reaction mass can be carried out by any isolation process known in the art, for example, cooling the reaction mass to a temperature of less than 35° C. followed by stirring and filtering. The wet solid obtained may be subjected to drying under vacuum at a temperature of about 75° C. to about 95° C. for sufficient period of time, preferably for 20 to 28 hours to obtain ivacaftor Form-L14.

The novel polymorphs of ivacaftor and solvates thereof described above are stable under ambient conditions; further novel polymorphs of ivacaftor and solvates thereof described above are having higher dissolution rate compared to known forms of ivacaftor and solvates thereof.

In another embodiment, the present invention provides a pharmaceutical composition comprising a therapeutically effective amount of novel polymorphs of ivacaftor described above, with at least one pharmaceutically acceptable carrier or other excipients. The pharmaceutical composition can be useful for the treatment of cystic fibrosis.

The present invention further provides, when a pharmaceutical composition comprising novel polymorphs of ivacaftor prepared according to the present invention is formulated for oral administration or parenteral administration. Accordingly, D50 and D90 particle size of the unformulated novel polymorphs of ivacaftor of the present invention used as starting material in preparing a pharmaceutical composition generally is less than 500 microns preferably less than about 300 microns, more preferably less than 100 microns.

Any milling, grinding, micronizing or other particle size reduction method known in the art can be used to bring the novel polymorphs of ivacaftor of the present invention into any desired particle size range as set forth above.

In accordance with the invention, novel polymorphs of ivacaftor can be embodied for example in form of tablet, capsules, pellets, granules and suppositories or their combined forms. In accordance with the present invention pharmaceutical compositions can be suitable for immediate release and modified release. Solid pharmaceutical compositions can be for example film coated or coated with aim of increasing pelletibility or regulating the disintegration or absorption.

Other embodiments of the invention include composition containing one or more polymorphic forms of ivacaftor described above, such as pharmaceutical dosage forms. Such pharmaceutical dosage forms may include one or more excipients, including, without limitation, diluents, disintegrants, surfactants, binders, glidants, lubricants, emulsifiers, suspending agents, sweeteners, flavourings, preservatives, buffers, wetting agents, effervescent agents, and other conventional excipients and additives. The compositions of the pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to humans without causing deleterious side effects or interactions.

Unless defined otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described.

EXAMPLES

The following non limiting examples illustrate specific embodiments of the present invention. They are not intended to be limiting the scope of the present invention in any way.

Example 1: Preparation of Ivacaftor Form-L1

A suspension of ivacaftor ethanolate (5 g) in n-heptane (200 mL) was heated to 95-100° C. and stirred for 5 hrs at the same temperature. Then the reaction mixture was cooled to 25-35° C. and stirred for an hour. The solid obtained was filtered, washed with n-heptane and suck dried. The wet solid was further dried at 60-65° C. for 16 hrs under vacuum yielded ivacaftor Form-L1. The XRPD is set forth in FIG. 1.

In a similar manner, ivacaftor Form-L1 was prepared from different solvates of ivacaftor in place of ivacaftor ethanolate as input using the following conditions;

| Input (Qty) | Solvent (Qty) | Drying temp/time |
|---|---|---|
| Ivacaftor diisopropyl ether (1.5 g) | n-heptane (60 mL) | 50° C./8 hr |
| Ivacaftor propanolate (1 g) | n-heptane (40 mL) | 50° C./8 hr |
| Ivacaftor cyclopentyl methyl ether (0.5 g) | n-heptane (20 mL) | 50° C./8 hr |
| Ivacaftor methyltertiarybutyl ether (0.5 g) | n-heptane (20 mL) | 50° C./8 hr |

Example 2: Preparation of Ivacaftor Form-L2

A suspension of ivacaftor ethanolate (5 g) in n-heptane (200 mL) was heated to 95-100° C. and stirred for 5 hrs at the same temperature. Then the reaction mixture was cooled to 25-35° C. and stirred for an hour. The obtained solid was filtered, washed with n-heptane and suck dried. The wet solid was further dried at 90-95° C. for 16 hrs under vacuum yielded ivacaftor Form-L2. The XRPD is set forth in FIG. 4

Example 3: Preparation of Ivacaftor Form-L2

A suspension of ivacaftor ethanolate (20 g) in n-heptane (800 mL) was heated to 95-100° C. and stirred for 5 hrs at the same temperature. Then the reaction mixture was cooled to 25-35° C. and stirred for an hour. The obtained solid was filtered, washed with n-heptane and suck dried. The wet solid was dried at 25-35° C. under vacuum for 24 hrs, which was further dried at 62° C. for 6 hrs and then at 90° C. for 30 hrs under vacuum to obtain ivacaftor Form-L2.

Example 4: Preparation of Ivacaftor Form-L3

Ivacaftor ethanolate (5 g) was dissolved in a mixture of acetonitrile (150 mL) and methanesulfonic acid (1.1 g) at 25-35° C. To this solution, water (112 mL) was added and the suspension was stirred for 2 hrs at 25-35° C. The obtained solid was filtered, washed with water and suck dried. The wet solid was further dried at 25-35° C. under vacuum for 16 hrs yielded ivacaftor Form-L3. The XRPD is set forth in FIG. 7

Example 5: Preparation of Ivacaftor Form-L4

Ivacaftor ethanolate (5 g) was dissolved in a mixture of acetonitrile (150 mL) and methanesulfonic acid (1.1 g) at 25-35° C. To this solution, water (112 mL) was added and the suspension was stirred for 2 hrs at 25-35° C. The obtained solid was filtered, washed with water and suck dried. The wet solid was further dried at 25-35° C. under vacuum for 24 hrs yielded ivacaftor Form-L4. The XRPD is set forth in FIG. 10.

Example 6: Preparation of Ivacaftor Form-L5

Ivacaftor ethanolate (5 g) was dissolved in a mixture of acetonitrile (150 mL) and methanesulfonic acid (1.1 g) at 25-35° C. To this solution, water (112 mL) was added and the suspension was stirred for 2 hrs at 25-35° C. The obtained solid was filtered, washed with water and suck dried. The wet solid was further dried at 60-65° C. under vacuum for 16 hrs yielded ivacaftor Form-L5. The XRPD is set forth in FIG. 13.

Example 7: Preparation of Ivacaftor Form-L6

Ivacaftor ethanolate (5 g) was dissolved in a mixture of acetonitrile (150 mL) and methanesulfonic acid (1.1 g) at 25-35° C. To this solution, water (112 mL) was added and the suspension was stirred for 2 hrs at 25-35° C. The obtained solid was filtered, washed with water and suck dried. The wet solid was further dried at 60-65° C. under vacuum for 24 hrs yielded ivacaftor Form-L6. The XRPD is set forth in FIG. 16.

Example 8: Preparation of Ivacaftor Form-L7

Ivacaftor ethanolate (5 g) was dissolved in a mixture of acetonitrile (150 mL) and methanesulfonic acid (1.1 g) at 25-35° C. To this solution, water (112 mL) was added and the suspension was stirred for 2 hrs at 25-35° C. The obtained solid was filtered, washed with water and suck dried. The wet solid was further dried at 90-100° C. under vacuum for 8 hrs yielded ivacaftor Form-L7. The XRPD is set forth in FIG. 19.

Example 9: Preparation of Ivacaftor Form-L8

A suspension of ivacaftor ethanolate (0.5 g) in cyclohexane (20 mL) was heated to 75-80° C. and stirred for 5 hrs at the same temperature. Then the reaction mixture was cooled to 25-35° C. and stirred for an hour. The solid obtained was filtered, washed with cyclohexane and suck dried. The wet solid was further dried at 40-45° C. under vacuum for 5 hrs yielded ivacaftor Form-L8. The XRPD is set forth in FIG. 22.

Example 10: Preparation of Ivacaftor Form-L8

A suspension of ivacaftor monohydrate (0.5 g) in cyclohexane (20 mL) was heated to 75-80° C. and stirred for 5 hrs at the same temperature. Then the reaction mixture was cooled to 25-35° C. and stirred for 30 mins. The solid obtained was filtered, washed with cyclohexane and suck dried. The wet solid was further dried at 40-45° C. for 5 hrs under vacuum yielded ivacaftor Form-L8.

Example 11: Preparation of Ivacaftor Form-L9

A suspension of ivacaftor monohydrate (0.5 g) in diisopropyl ether (20 mL) was heated to 65-70° C. and stirred for 5 hrs at the same temperature. Then the reaction mixture was cooled to 25-35° C. and stirred for 30 mins. The solid obtained was filtered, washed with diisopropylether and suck dried. The wet solid was further dried at 40-45° C. for 5 hrs under vacuum yielded ivacaftor Form-L9. The XRPD is set forth in FIG. 25.

Example 12: Preparation of Ivacaftor Form-L9

A suspension of ivacaftor ethanolate (5 g) in diisopropyl ether (200 mL) was heated to 65-70° C. and stirred for 5 hrs at the same temperature. Then the reaction mixture was cooled to 25-35° C. and stirred for an hour. The solid obtained was filtered, washed with diisopropylether and suck dried. The wet solid was further dried at 25-35° C. under vacuum for 14 hrs yielded ivacaftor Form-L9.

Example 13: Preparation of Ivacaftor Form-L10

A suspension of ivacaftor monohydrate (0.5 g) in n-propanol (20 mL) was heated to 95-100° C. and stirred for 1 hr at the same temperature. Then the reaction mixture was cooled to 25-35° C. and stirred for an hour. The solid obtained was filtered, washed with n-propanol and suck dried. The wet solid was further dried at 40-45° C. under vacuum for 5 hrs yielded ivacaftor Form-L10. The XRPD is set forth in FIG. 26.

Example 14: Preparation of Ivacaftor Form-L10

A suspension of ivacaftor ethanolate (5 g) in n-propanol (70 mL) was heated to 95-100° C. and stirred for 5 hrs at the same temperature. Then the reaction mixture was cooled to 25-35° C. and stirred for an hour. The solid obtained was filtered, washed with n-propanol and suck dried. The wet solid was further dried at 60-65° C. under vacuum for 14 hrs yielded ivacaftor Form-L10.

Example 15: Preparation of Ivacaftor Form-L11

A suspension of ivacaftor ethanolate (1 g) in methyl tertiarybutyl ether (40 mL) was heated to 50-55° C. and stirred for 5 hrs at the same temperature. Then the reaction mixture was cooled to 25-35° C. and stirred for an hour. The solid obtained was filtered, washed with methyl tertiarybutyl ether and suck dried. The wet solid was further dried at 90-95° C. under vacuum for 4 hrs yielded ivacaftor Form-L11. The XRPD is set forth in FIG. 27.

Example 16: Preparation of Ivacaftor Form-L11

A suspension of ivacaftor ethanolate (1 g) in methyl tertiarybutyl ether (40 mL) was heated to 50-55° C. and stirred for 5 hrs at the same temperature. Then the reaction mixture was cooled to 25-35° C. and stirred for an hour. The solid obtained was filtered, washed with methyl tertiarybutyl ether and suck dried. The wet solid was further dried at 25-35° C. for 24 hrs under vacuum yielded ivacaftor Form-L11.

Example 17: Preparation of Ivacaftor Form-L12A

A suspension of ivacaftor ethanolate (0.5 g) in cyclopentylmethylether (20 mL) was heated to 95-100° C. and stirred for 5 hrs at the same temperature. Then the reaction mixture was cooled to 25-35° C. and stirred for an hour. The solid obtained was filtered, washed with cyclopentylmethylether and suck dried. The wet solid was further dried at 40-45° C. for 5 hrs under vacuum yielded ivacaftor Form-L12A. The XRPD is set forth in FIG. 28.

Example 18: Preparation of Ivacaftor Form-L12B

A suspension of ivacaftor ethanolate (5 g) in cyclopentylmethyl ether (200 mL) was heated to 95-100° C. and stirred for 5 hrs at the same temperature. Then the reaction mixture was cooled to 25-35° C. and stirred for an hour. The solid obtained was filtered, washed with cyclopentylmethylether and suck dried. The wet solid was further dried at 25-35° C. for 14 hrs under vacuum yielded ivacaftor Form-L12B. The XRPD is set forth in FIG. 29.

Example 19: Preparation of Ivacaftor Form-L13

A suspension of ivacaftor ethanolate (1 g) in hexane (40 mL) was heated to 65-70° C. and stirred for 5 hrs at the same temperature. Then the reaction mixture was cooled to 25-35° C. and stirred for an hour. The solid obtained was filtered, washed with hexane and suck dried. The wet solid was further dried at 25-35° C. for 24 hrs under vacuum yielded ivacaftor Form-L13. The XRPD is set forth in FIG. 30.

Example 20: Preparation of Ivacaftor Form-L14

A suspension of ivacaftor ethanolate (1 g) in hexane (40 mL) was heated to 65-70° C. and stirred for 5 hrs at the same temperature. Then the reaction mixture was cooled to 25-35° C. and stirred for an hour. The solid obtained was filtered, washed with hexane and suck dried. The wet solid was further dried at 90-95° C. for 24 hrs under vacuum yielded ivacaftor Form-L14. The XRPD is set forth in FIG. 31.

Example 21

The following stability study data tables at different storage condition ensures that the ivacaftor Form-L2 of the present invention retained the same polymorphic and chemical identity at least up to three months.

Ivacaftor Form L2 is packed in a transparent Low density polyethylene (LDPE) bag with a strip seal, which is again kept in a second transparent low density polyethylene bag with strip seal. The LDPE bag is kept in to a triple laminated sunlight barrier with heat seal followed by in a high density polyethylene container and well closed.

TABLE I

Chemical and polymorphic stability data of Ivacaftor Form-L2 when stored at 25 ± 2° C./60 ± 5% RH:

| Parameters | Initial (% by HPLC) | 1 month (% by HPLC) | 3 month (% by HPLC) |
| --- | --- | --- | --- |
| Description | off-white colour solid | off-white colour solid | off-white colour solid |
| Ivacaftor ortho isomer (Imp-1) | ND | ND | ND |
| De-alkylated ivacaftor (Imp-2) | ND | ND | ND |

TABLE I-continued

Chemical and polymorphic stability data of Ivacaftor Form-L2 when stored at 25 ± 2° C./60 ± 5% RH:

| Parameters | Initial (% by HPLC) | 1 month (% by HPLC) | 3 month (% by HPLC) |
|---|---|---|---|
| Quinolone acid (Imp-3) | 0.01 | ND | ND |
| Impurity at RRT 0.59 | ND | ND | ND |
| Any major unknown impurity | 0.02 | 0.02 | 0.02 |
| Total impurity | 0.03 | 0.02 | 0.02 |
| Solid form by XRD | Complies | Complies | Complies |

ND: Not detected;
LOD of Imp-1: 0.04% by HPLC;
LOD of Imp-2: 0.02% by HPLC & LOD of Imp-3: 0.006% by HPLC

TABLE II

Chemical and polymorphic stability data of Ivacaftor Form-L2 when stored at 40 ± 2° C./75 ± 5% RH:

| Parameters | Initial (% by HPLC) | 1 month (% by HPLC) | 3 month (% by HPLC) |
|---|---|---|---|
| Description | off-white colour solid | off-white colour solid | off-white colour solid |
| Ivacaftor ortho isomer (Imp-1) | ND | ND | ND |
| De-alkylated ivacaftor (Imp-2) | ND | ND | ND |
| Quinolone acid (Imp-3) | ND | ND | ND |
| Impurity at RRT 0.59 | 0.01 | ND | ND |
| Any major unknown impurity | 0.02 | 0.01 | 0.01 |
| Total impurity | 0.03 | 0.03 | 0.03 |
| Solid form by XRD | Complies | Complies | Complies |

ND: Not detected;
LOD of Imp-1: 0.04% by HPLC;
LOD of Imp-2: 0.02% by HPLC & LOD of Imp-3: 0.006% by HPLC;
Imp-1: N-[3,5-di(tert-butyl)-2-hydroxyphenyl]-4-oxo-1,4-dihydro-3-quinoline carboxamide; Imp-2: N-[4-(tert-butyl)-3-hydroxyphenyl]-4-oxo-1,4-dihydro-3-quinolinecarboxamide & Imp-3: 4-Oxo-1,4-dihydroquinonline-3-carboxylic acid.

The ivacaftor was analyzed using High Performance Liquid Chromatography ("HPLC") with the conditions are tabulated below:

| | |
|---|---|
| Column | Symmetry C18, (150 × 4.6) mm, 5 μm |
| Column temp | 35° C. |
| Mobile phase | A: orthophosphoric acid; B: Acetonitrile and water |
| Diluent | Acetonitrile and water |
| Flow rate | 1 ml/min |
| Wavelength | 235 nm |
| Injection Volume | 10 μl |

Example 22

Saturation solubility studies were conducted in various mediums for ivacaftor polymorph Form-L2 and Amorphous form and the data is given in Table III.

TABLE III

Comparative Saturation Solubility data of Polymorphic Form-L2 & Amorphous form

| | | | Solubility (mg/mL) | |
|---|---|---|---|---|
| Sr. No | Medium | pH | Form-L2 | Amorphous form |
| 1 | 0.1N HCl + 0.7% SLS | 1.10 | 0.15 | 0.12 |
| 2 | 0.01N HCl + 0.7% SLS | 2.12 | 0.26 | 0.18 |
| 3 | 0.001N HCl + 0.7% SLS | 3.12 | 0.24 | 0.23 |
| 4 | pH 4.5 AB + 0.7% SLS | 4.52 | 0.31 | 0.17 |
| 5 | 50 mM Phosphate buffer + 0.7% SLS | 4.60 | 0.38 | 0.19 |
| 6 | pH 5.5 PB + 0.7% SLS | 5.53 | 0.26 | 0.18 |
| 7 | pH 6.8 PB + 0.7% SLS | 6.80 | 0.26 | 0.18 |

From the above data it is observed that novel polymorphic Form-L2 shows more solubility when compared to amorphous form.

Example 23

Tablet composition using Ivacaftor polymorphic Form-L2, & Amorphous form:

| S. No. | Ingredients | Form-L2 (% wt/wt) | Amorphous form (% wt/wt) |
|---|---|---|---|
| 1 | Ivacaftor | 26.46 | 26.46 |
| 2 | Lactose monohydrate | 28.22 | 28.22 |
| 3 | Microcrystalline Cellulose | 27.78 | 27.78 |
| 4 | Croscarmellose Sodium | 7.76 | 7.76 |
| 5 | Hypromellose | 4.85 | 4.85 |
| 6 | Sodium lauryl sulfate | 0.97 | 0.97 |
| 7 | Colloidal silicon dioxide | 0.49 | 0.49 |
| 8 | Magnesium stearate | 0.49 | 0.49 |
| 9 | Opadry II Blue 85F90614 | 3.00 | 3.00 |
| | Total Weight | 100.00 | 100.00 |

Process:

Core tablets are prepared using direct compression process and are then film-coated with aqueous coating.

In-vitro drug release by dissolution using 50 mM Sodium Phosphate buffer with 0.7% SLS as dissolution medium, USP Type II, rotation speed of 65 rpm in 900 mL was performed for the above tablets and comparative data is given in Table IV. More than 85% of drug was released within in 15 minutes when the composition using Ivacaftor Form L2 whereas less than 70% drug release was observed with the amorphous form.

TABLE IV

Dissolution profile of ivacaftor tablets:

| | % ivacaftor release | |
|---|---|---|
| Time in minutes | Tablets prepared using Ivacaftor Polymorphic Form-L2 | Tablets prepared using Ivacaftor Amorphous form |
| 5 | 70 | 38 |
| 10 | 86 | 47 |
| 15 | 91 | 68 |
| 20 | 93 | 77 |
| 30 | 95 | 89 |
| 45 | 98 | 93 |
| 60 | 100 | 98 |

We claim:
1. An ivacaftor Form-L2 polymorph characterized by a powder X-Ray diffraction pattern having one or more peaks at about 5.6, 7.0, 13.1, 13.4, 14.1, 15.2, 16.8, 20, 20.4, 24.4 and 28.5±0.2° 2θ.
2. The ivacaftor Form-L2 of claim 1, further characterized by a powder X-Ray diffraction pattern substantially in accordance with FIG. 4, a differential scanning calorimetry curve substantially in accordance with FIG. 5 or a thermo gravimetric analysis (TGA) result substantially in accordance with FIG. 6.
3. A process for the preparation of the ivacaftor Form-L2 of claim 1, comprising:
   a) suspending or mixing ivacaftor in n-heptane;
   b) heating the suspension;
   c) isolating the solid; and
   d) drying the solid at about 85° C. to about 95° C.
4. The process of claim 3, wherein the ivacaftor of step a) is ivacaftor ethanol solvate,
   wherein the heating step b) is carried out at a temperature of about 60° C. to reflux temperature,
   wherein the step c) further comprises the steps of i) cooling the suspension of step b) to less than 35° C. and ii) filtering the suspension, and
   wherein the drying of step d) is carried out for a time period of about 16 to 30 hours.
5. An ivacaftor Form-L1 polymorph characterized by a powder X-Ray diffraction pattern having one or more peaks at about 5.48, 5.74, 6.46, 8.12, 8.56, 9.82, 10.28, 11.00, 11.70, 13.40, 13.90, 14.38, 15.22, 15.64, 16.38, 16.64, 17.30, 17.80, 18.24, 18.96, 19.22, 20.62, 20.86, 21.12, 21.74, 21.98, 23.06, 23.96, 24.82, 25.30, 25.94, 26.82, 28.08, 28.48 and 30.34±0.2° 2θ.
6. The ivacaftor Form-L1 of claim 5, further characterized by a powder X-Ray diffraction pattern substantially in accordance with FIG. 1, a differential scanning calorimetry curve substantially in accordance with FIG. 2, or a thermo gravimetric analysis (TGA) result substantially in accordance with FIG. 3.
7. A process for the preparation of the ivacaftor Form-L1 of claim 5, comprising:
   a) suspending or mixing ivacaftor in n-heptane;
   b) heating the suspension;
   c) isolating the solid; and
   d) drying the solid at about 45° C. to about 65° C.
8. An ivacaftor Form-L3 polymorph characterized by a powder X-Ray diffraction pattern having one or more peaks at about 5.70, 7.96, 10.36, 11.22, 12.88, 14.10, 15.60, 17.34, 18.14, 18.80, 19.84, 20.90, 22.48, 23.68, 24.64, 25.62 and 28.00±0.2° 2θ.
9. The ivacaftor Form-L3 of claim 8, further characterized by a powder X-Ray diffraction pattern substantially in accordance with FIG. 7, a differential scanning calorimetry curve substantially in accordance with FIG. 8, or a thermo gravimetric analysis (TGA) result substantially in accordance with FIG. 9.
10. A process for preparation of the ivacaftor Form-L3 of claim 8, comprising:
   a) dissolving ivacaftor in a mixture of acetonitrile and an acid;
   b) adding water to the step a) solution at about 25° C. to about 35° C.;
   c) isolating the solid; and
   d) drying the solid obtained in step c) at about 25° C. to about 35° C. for about 16 hours.
11. The process of claim 10, wherein the acid is selected from acetic acid, methanesulfonic acid, and mixtures thereof, and wherein dissolving the ivacaftor in the acid is done at a temperature of about 25° C. to about 45° C.
12. An ivacaftor Form-L4 polymorph characterized by a powder X-Ray diffraction pattern having one or more peaks at about 5.74, 8.26, 10.68, 11.56, 13.30, 14.60, 15.76, 17.88, 21.02, 22.90, 23.78, 25.14, 25.94, 28.20 and 29.98±0.2° 2θ.
13. The ivacaftor Form-L4 of claim 12, further characterized by a powder X-Ray diffraction pattern substantially in accordance with FIG. 10, a differential scanning calorimetry curve substantially in accordance with FIG. 11, or a thermo gravimetric analysis result substantially in accordance with FIG. 12.
14. A process for preparation of the ivacaftor Form-L4 of claim 12, comprising:
   a) dissolving ivacaftor in a mixture of acetonitrile and an acid;
   b) adding water to the step a) solution at about 25° C. to about 35° C.;
   c) isolating the solid; and
   d) drying the solid obtained in step c) at about 25° C. to about 35° C. for about 24 hours.
15. The process of claim 14, wherein the suitable acid is selected from acetic acid, methanesulfonic acid, and mixtures thereof.
16. An ivacaftor Form-L5 polymorph characterized by a powder X-Ray diffraction pattern having one or more peaks at about 5.78, 6.42, 8.08, 10.18, 11.24, 12.90, 14.02, 14.34, 15.52, 17.40, 18.38, 19.28, 20.90, 22.60, 23.84, 24.76, 25.82, 27.16, 28.00 and 29.86±0.2° 2θ.
17. Ivacaftor Form-L5 of claim 16, further characterized by a powder X-Ray diffraction (PXRD) pattern substantially in accordance with FIG. 13, a differential scanning calorimetry (DSC) substantially in accordance with FIG. 14, or a thermo gravimetric analysis (TGA) substantially in accordance with FIG. 15.
18. A process for preparation of the ivacaftor Form-L5 of claim 16, comprising:
   a) dissolving ivacaftor in a mixture of acetonitrile and an acid;
   b) adding water to the step a) solution at about 25° C. to about 35° C.;
   c) isolating the solid; and
   d) drying the solid obtained in step c) at about 55° C. to about 65° C. for about 16 hours.
19. The process of claim 18, wherein the acid is selected from acetic acid, methanesulfonic acid, and mixtures thereof.
20. An ivacaftor Form-L6 polymorph characterized by a powder X-Ray diffraction pattern having one or more peaks at about 6.38, 7.32, 8.10, 9.94, 11.12, 12.84, 14.64, 15.56, 17.44, 19.28, 20.66, 21.46, 25.46 and 29.62±0.2° 2θ.
21. The ivacaftor Form-L6 of claim 20, further characterized by a powder X-Ray diffraction pattern substantially in accordance with FIG. 16, a differential scanning calorimetry curve substantially in accordance with FIG. 17, or a thermo gravimetric analysis result substantially in accordance with FIG. 18.
22. A process for preparation of the ivacaftor Form-L6 of claim 20, comprising:
   a) dissolving ivacaftor in a mixture of acetonitrile and an acid;
   b) adding water to the step a) solution at 25° C. to about 35° C.;
   c) isolating the solid; and
   d) drying the solid obtained in step c) at about 55° C. to about 65° C. for 24 hours.

23. The process of claim 22, wherein the acid is selected from acetic acid, methanesulfonic acid, and mixtures thereof.

24. An ivacaftor Form-L7 polymorph characterized by a powder X-Ray diffraction pattern having one or more peaks at about 5.0, 7.32, 8.46, 10.08, 12.38, 13.66, 15.62, 16.54, 18.58, 20.18, 21.88, 22.36, 23.00, 24.30, 24.80, 25.12, 25.64, 26.30, 26.54, 27.60, 28.06 and 29.30±0.2° 2θ.

25. The ivacaftor Form-L7 of claim 24, further characterized by a powder X-Ray diffraction pattern substantially in accordance with FIG. 19, a differential scanning calorimetry curve substantially in accordance with FIG. 20, or a thermo gravimetric analysis result substantially in accordance with FIG. 21.

26. A process for preparation of the ivacaftor Form-L7 of claim 24, comprising:
   a) dissolving ivacaftor in a mixture of acetonitrile and an acid;
   b) adding water to the step a) solution at 25° C. to about 35° C.;
   c) isolating the solid; and
   d) drying the solid obtained in step c) at about 75° C. to about 100° C. to obtain the ivacaftor Form-L7.

27. The process of claim 26, wherein the acid is selected from acetic acid, methanesulfonic acid, and mixtures thereof.

28. An ivacaftor Form-L8 polymorph characterized by a powder X-Ray diffraction pattern having one or more peaks at about 4.86, 7.84, 8.24, 9.70, 11.56, 13.98, 15.26, 15.62, 16.34, 16.70, 17.40, 18.10, 19.60, 20.72, 21.16, 22.40, 23.66, 24.96, 26.30, 28.72, 30.14 and 31.76±0.2° 2θ.

29. The ivacaftor Form-L8 of claim 28, further characterized by a powder X-Ray diffraction pattern substantially in accordance with FIG. 22, a differential scanning calorimetry curve substantially in accordance with FIG. 23, or a thermo gravimetric analysis result substantially in accordance with FIG. 24.

30. A process for the preparation of the ivacaftor Form-L8 of claim 28, comprising:
   a) suspending or mixing ivacaftor in cyclohexane;
   b) heating the suspension;
   c) isolating the solid; and
   d) drying the solid to obtain the ivacaftor Form-L8.

31. An ivacaftor Form-L9 characterized by a powder X-Ray diffraction pattern having one or more peaks at about 5.86, 6.84, 8.50, 10.18, 11.48, 11.96, 13.82, 14.84, 15.66, 16.74, 17.12, 18.28, 18.66, 19.50, 21.02, 21.30, 22.06, 22.42, 23.20, 25.16, 25.50, 27.02, 28.44, 30.74 and 32.84±0.2° 2θ.

32. The ivacaftor Form-L9 of claim 31, further characterized by a powder X-Ray diffraction pattern substantially in accordance with FIG. 25.

33. A process for the preparation of the ivacaftor Form-L9 of claim 31, comprising:
   a) suspending or mixing ivacaftor in diisopropylether;
   b) heating the suspension;
   c) isolating the solid; and
   d) drying the solid to obtain ivacaftor Form-L9.

34. An ivacaftor Form-L10 polymorph characterized by a powder X-Ray diffraction pattern having one or more peaks at about 5.98, 8.26, 9.94, 10.92, 12.10, 12.54, 13.24, 13.98, 14.74, 15.36, 17.42, 17.96, 18.24, 18.66, 19.38, 19.80, 20.24, 22.38, 23.54, 24.46, 25.98, 26.86, 27.76, 29.30, 30.74, 32.02, 35.30 and 38.22±0.2° 2θ.

35. The ivacaftor Form-L10 of claim 34, further characterized by a powder X-Ray diffraction pattern substantially in accordance with FIG. 26.

36. A process for the preparation of the ivacaftor Form-L10 of claim 34, comprising:
   a) suspending or mixing ivacaftor in n-propanol;
   b) heating the suspension;
   c) isolating the solid; and
   d) drying the solid to obtain the ivacaftor Form-L10.

37. An ivacaftor Form-L11 polymorph characterized by a powder X-Ray diffraction pattern having one or more peaks at about 4.66, 8.08, 8.46, 9.46, 11.30, 13.70, 14.98, 15.36, 16.26, 17.50, 17.90, 19.24, 20.44, 20.86, 22.16, 23.38, 24.64, 25.94, 29.04 and 31.60±0.2° 2θ.

38. The ivacaftor Form-L11 of claim 37, further characterized by a powder X-Ray diffraction pattern substantially in accordance with FIG. 27.

39. A process for the preparation of the ivacaftor Form-L11 of claim 37, comprising:
   a) suspending or mixing ivacaftor in methyl tertiary butyl ether;
   b) heating the suspension;
   c) isolating the solid; and
   d) drying the solid to obtain ivacaftor Form-L11.

40. An ivacaftor Form-L12A polymorph characterized by a powder X-Ray diffraction pattern having one or more peaks at about 4.18, 8.56, 11.32, 12.96, 15.04, 15.18, 17.62, 18.76, 20.28, 21.06, 23.00 and 26.22±0.2° 2θ.

41. The ivacaftor Form-L12A of claim 40, further characterized by a powder X-Ray diffraction pattern substantially in accordance with FIG. 28.

42. A process for the preparation of the ivacaftor Form-L12A of claim 40, comprising:
   a) suspending or mixing ivacaftor in cyclopentyl methyl ether;
   b) heating the suspension;
   c) isolating the solid; and
   d) drying the solid at about 40° C. to about 50° C.

43. An ivacaftor Form-L12B polymorph characterized by a powder X-Ray diffraction pattern having one or more peaks at about 4.46, 6.96, 7.88, 8.78, 10.88, 11.52, 11.80, 14.16, 15.84, 16.72, 17.50, 18.30, 18.88, 19.64, 20.52, 21.32, 23.46, 24.88, 27.52 and 28.64±0.2° 2θ.

44. The ivacaftor Form-L12B of claim 43, further characterized by a powder X-Ray diffraction pattern substantially in accordance with FIG. 29.

45. A process for the preparation of the ivacaftor Form-L12B of claim 43, comprising:
   a) suspending or mixing ivacaftor in cyclopentyl methyl ether;
   b) heating the suspension;
   c) isolating the solid; and
   d) drying the solid at about 25° C. to about 35° C.

46. An ivacaftor Form-L13 polymorph characterized by a powder X-Ray diffraction pattern having one or more peaks at about 4.72, 8.16, 9.50, 11.38, 13.78, 15.10, 15.46, 16.36, 17.70, 17.94, 19.36, 20.52, 22.32, 23.46, 24.72, 26.10, 29.16 and 31.64±0.2° 2θ.

47. The ivacaftor Form-L13 of claim 46, further characterized by a powder X-Ray diffraction pattern substantially in accordance with FIG. 30.

48. A process for the preparation of the ivacaftor Form-L13 of claim 46, comprising:
   a) suspending or mixing ivacaftor in n-hexane;
   b) heating the suspension;
   c) isolating the solid; and
   d) drying the solid at about 25° C. to about 35° C.

49. An ivacaftor Form-L14 polymorph characterized by a powder X-Ray diffraction pattern having one or more peaks at about 4.98, 8.04, 8.50, 9.82, 11.84, 14.18, 15.38, 16.64, 17.74, 18.42, 19.72, 21.00, 22.82, 23.84, 25.14, 26.38, 28.88, 32.04±0.2° 2θ.

50. The ivacaftor Form-L14 of claim 49, further characterized by a powder X-Ray diffraction pattern substantially in accordance with FIG. 31.

51. A process for the preparation of the ivacaftor Form-L14 of claim 49, comprising:
   a) suspending or mixing ivacaftor in n-hexane;
   b) heating the suspension;
   c) isolating the solid; and
   d) drying the solid at about 85° C. to about 95° C.

52. A pharmaceutical composition comprising a therapeutically effective amount of one of ivacaftor Form-L1, Form-L2, Form-L3, Form-L4, Form-L5, Form-L6, Form-L7, Form-L8, Form-L9, Form-L10, Form-L11, Form-L12A, Form-L12B, Form-L13, and Form-L14, and at least one pharmaceutically acceptable carrier or excipient.

* * * * *